United States Patent
Koike et al.

(10) Patent No.: US 7,202,093 B2
(45) Date of Patent: Apr. 10, 2007

(54) METHOD FOR LABELING PHOSPHORYLATED PEPTIDES, METHOD FOR SELECTIVELY ADSORBING PHOSPHORYLATED PEPTIDES, COMPLEX COMPOUNDS USED IN THE METHODS, PROCESS FOR PRODUCING THE COMPLEX COMPOUNDS, AND RAW MATERIAL COMPOUNDS FOR THE COMPLEX COMPOUNDS

(75) Inventors: Tohru Koike, Hiroshima (JP); Akihiko Kawasaki, Amagasaki (JP); Tatsuhiro Kobashi, Amagasaki (JP); Makoto Takahagi, Amagasaki (JP)

(73) Assignee: Kabushiki Kaisha Nard Kenkyusho (JP)

( * ) Notice: Subject to any disclaimer, the term of this patent is extended or adjusted under 35 U.S.C. 154(b) by 216 days.

(21) Appl. No.: 10/784,576

(22) Filed: Feb. 23, 2004

(65) Prior Publication Data

US 2004/0198712 A1    Oct. 7, 2004

(30) Foreign Application Priority Data

| Mar. 3, 2003 | (JP) | ............................ 2003-056068 |
| Apr. 18, 2003 | (JP) | ............................ 2003-113707 |
| Oct. 16, 2003 | (JP) | ............................ 2003-356934 |

(51) Int. Cl.

| G01N 33/532 | (2006.01) |
| G01N 33/533 | (2006.01) |
| G01N 21/76 | (2006.01) |
| G01N 33/42 | (2006.01) |
| C07K 1/13 | (2006.01) |
| C07D 213/00 | (2006.01) |
| G01N 24/00 | (2006.01) |
| G01N 33/53 | (2006.01) |

(52) U.S. Cl. ...................... 436/544; 436/546; 436/172; 436/173; 436/81; 436/805; 436/815; 435/7.1; 435/7.5; 435/961; 530/402; 546/255

(58) Field of Classification Search ................ 436/544, 436/546, 533, 525, 81, 805, 172, 173, 815; 435/7.1, 961, 7.5; 546/285; 530/402

See application file for complete search history.

(56) References Cited

U.S. PATENT DOCUMENTS

| 5,874,584 A | 2/1999 | Wear et al. |
| 6,120,768 A * | 9/2000 | Griffiths et al. .......... 424/178.1 |
| 6,143,879 A | 11/2000 | Que, Jr. et al. |
| 2005/0038258 A1* | 2/2005 | Koike et al. ................ 546/285 |

FOREIGN PATENT DOCUMENTS

JP     2001-253871    9/2001

WO    WO 03/053932 A1 *    7/2003

OTHER PUBLICATIONS

Hidekazu Arii et al., A novel diiron complex as a functional model for hemerythrin, Journal of Inorganic Biochemistry, 82, pp. 153-162 (2000).

Yashiro, Morio et al., Preparation and study of dinuclear zinc (II) complex for the efficient hydrolysis of the phosphodiester linkage in a diribonucleotide, Journal of the Chemical Society, Chemical Communications, 1995, No. 17, p. 1793-4.

Yamaguchi, Kazuya et al., Hydrolysis of phosphodiester with hydroxo- or carboxylate-bridged dinuclear Ni (II) and Cu (II) complexes, Chemical Communications, Feb. 8, 2001, No. 4, pp. 375 to 376.

Nishino, Satoshi et al., Enhanced nucleophilicity and depressed electrophilicity of peroxide by zinc (II), aluminum (III) and lanthanum (II) ions, Zeitschrift fuer Naturforschung, C: Journal of Biosciences, Feb. 2001, vol. 56, No. 1/2, pp. 138 to 143.

Sato, Junjiro et al., Properties of chiral ce (III)—tppn complex as a chiral shift reagent in aqueous solution, Rare earths, 1998, No. 32, pp. 58 to 59.

Adams, Harry et al., Zinc (II) complexes of tetrapodal ligands derived from tetra-substituted 1, n-diaminoalcohols, Journal of the Chemical Society, Dalton Transactions, Feb. 21, 2002, No. 6, pp. 925 to 930.

* cited by examiner

*Primary Examiner*—Long V. Le
*Assistant Examiner*—Shafiqul Haq
(74) *Attorney, Agent, or Firm*—Gerald E. Hespos; Anthony J. Casella

(57) ABSTRACT

Provided are a method for easily detecting phosphorylated peptides, namely, proteins, in samples derived from living organisms or the like, a method for selectively adsorbing the phosphorylated peptides, and compounds that are highly coordinated to the phosphorylated peptides and usable in the methods. The complex compound is represented by the formula:

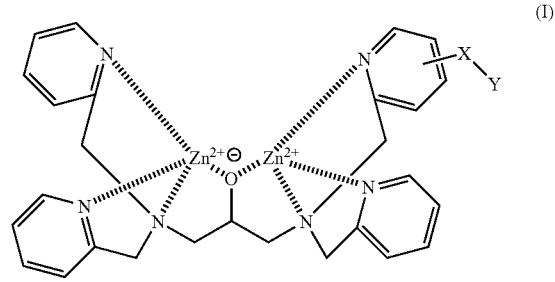

wherein X is a linker moiety, and Y is a labeling group. The compound (I) is highly coordinated to a phosphorylated peptide, and has a labeling group. Accordingly, with use of the compound (I), the phosphorylated peptide can be easily identified.

10 Claims, 9 Drawing Sheets

FIG.2
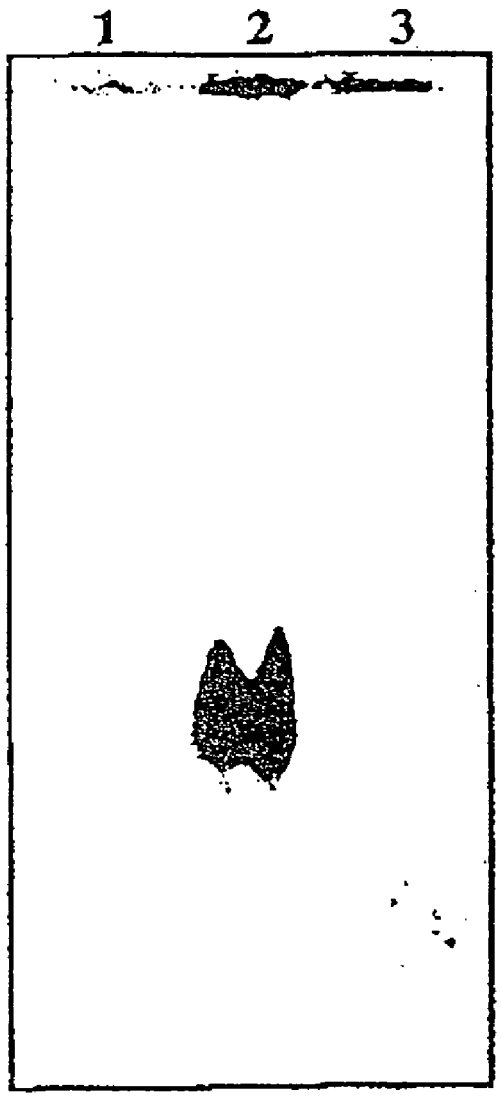
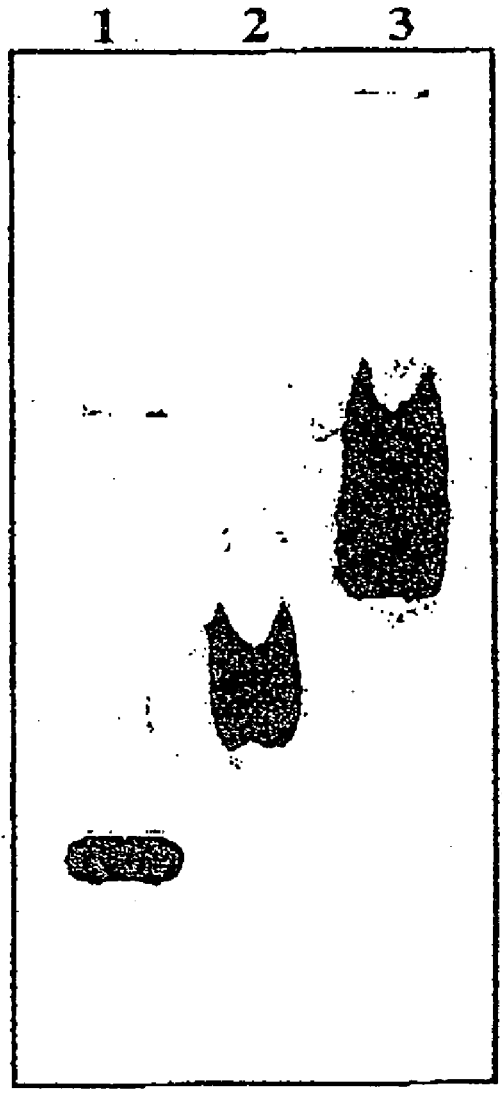

FIG. 9
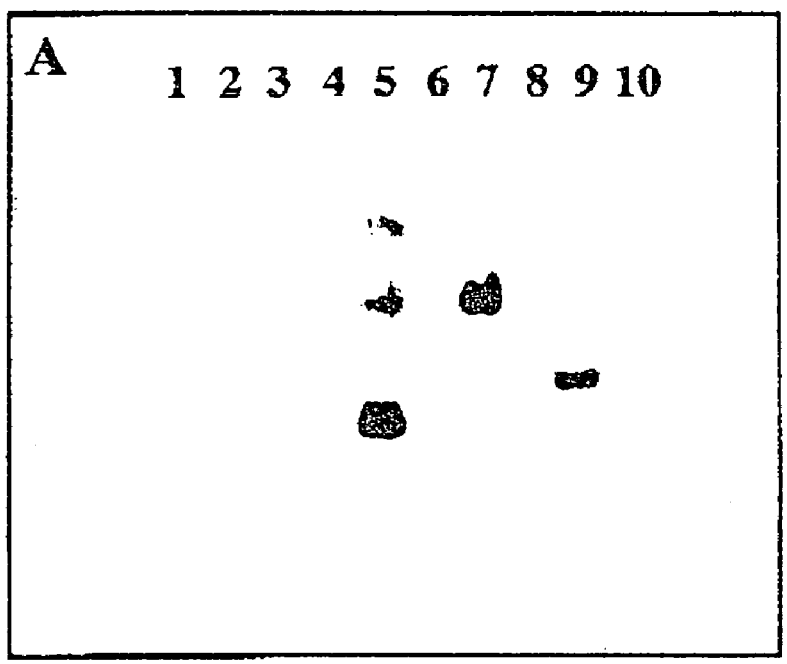
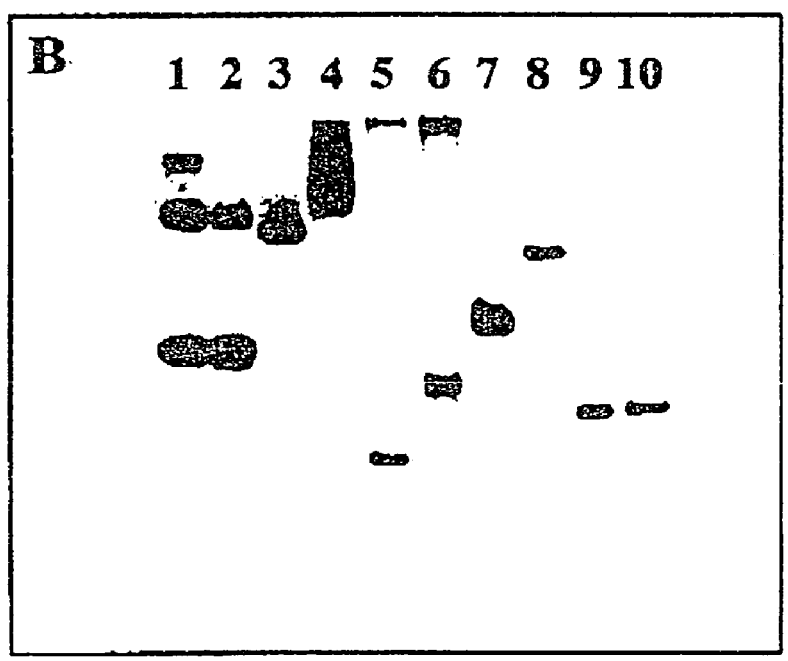

METHOD FOR LABELING PHOSPHORYLATED PEPTIDES, METHOD FOR SELECTIVELY ADSORBING PHOSPHORYLATED PEPTIDES, COMPLEX COMPOUNDS USED IN THE METHODS, PROCESS FOR PRODUCING THE COMPLEX COMPOUNDS, AND RAW MATERIAL COMPOUNDS FOR THE COMPLEX COMPOUNDS

BACKGROUND OF THE INVENTION

1. Field of the Invention

The present, invention relates to a method for labeling phosphorylated peptides, a method for selectively adsorbing phosphorylated peptides, complex compounds usable in the methods, a process for producing the complex compounds, and compounds usable as a raw material in the production process.

2. Description of the Related Art

There are known in vivo enzymes having serine, threonine or tyrosine residue at a specific site corresponding to an active center or allosteric site. The enzymatic activity of these enzymes is controlled by phosphorylating or dephosphorylating hydroxyl group in these residues by an enzyme called kinase and the like. Also, there are known enzymes whose enzymatic activity is controlled by phosphorylating or dephosphorylating an amino group or an imino group in lysin, arginine or histidine, or a carboxyl group in aspartic acids or glutamic acids.

One of the examples of the metabolic systems which are controlled by the aforementioned phosphorylation-dephosphorylation is a system of suppressing synthesis of glycogen and decomposing the same. This metabolic system is primarily cascade-controlled by the phosphorylation-dephosphorylation.

A recent study elucidated that the phosphorylation-dephosphorylation plays a significant role in disease-related metabolic systems.

For instance, it is said that one of the causes of cell carcinogenesis is abnormality in the phosphorylation-dephosphorylation. Specifically, progress and stop of cell cycle are controlled by phosphorylation or dephosphorylation of various enzymes, i.e., proteins. Cycline and cycline-dependent kinase (CDK) are relevant factors in the phosphorylation or dephosphorylation. If the mechanism relating to cycline and CDK is impaired, phosphorylation or dephosphorylation may be uncontrollable, thereby triggering abnormal proliferation of cells.

In addition to the above, facts are known that protein kinase C is related with degranulation of histamine causative of allergic disorders such as atopic dermatitis and pollen allergy, and that phosphorylated tau-protein is causative of neurofibrillary tangle in the brains of Alzheimer's patients.

In view of the above, comprehending the condition of phosphorylation-dephosphorylation of proteins provides useful measures not only in investigating expression of genes in living tissue cells and evaluating the enzymatic activity of the cells, but also in diagnosing diseases or medical treatment.

The conventional methods for identifying phosphorylated proteins or dephosphorylated proteins have various drawbacks.

For instance, while an enzyme immunoassay is advantageous in analyzing a target protein sample of a very small amount, it is difficult to obtain antibodies of the target protein of a sufficient amount. Further, in case that the level of the target protein is several kDa or lower, it is impossible to prepare an antibody that is securely bonded to a site in the protein where phosphorylation occurs.

There is proposed a method for detecting a protein specifically bonded by a phosphoric acid with use of a phosphoric acid labeled with a radioactive isotope $^{32}P$. However, special attention should be paid in handling radioactive isotopes, and appropriate administration and disposal of waste liquid of the radioactive isotopes are required.

There is proposed an idea of applying two-dimensional electrophoresis in view of the fact that electric charges are differentiated between phosphorylated proteins and dephosphorylated proteins. However, it is extremely difficult to identify the band or spot of a phosphorylated or dephosphorylated protein in analyzing a sample derived from a living organism, because the sample contains a variety of proteins. Furthermore, use of a radioactive isotope to identify the band or spot involves the aforementioned problems.

The document, Morio YASHIRO, et al. [Preparation and Study of Dinuclear Zinc(II) Complex for the Efficient Hydrolysis of the Phosphodiester Linkage in a Diribonucleotide], Journal of the Chemical Society, Chemical communications. pp. 1793–1794 (1995), recites a zinc complex. The zinc complex has a function that two zinc ions in the complex dissociate a phosphoric acid group, namely, phosphoric diester, from dinucleotide. However, the function of the zinc complex disclosed in the document is merely a catalyst. The document dose not disclose the ability of the zinc complex to bond coordinately to a phosphoric acid group. The experiments conducted by the inventors reveal that a dissociation constant of the zinc complex to a phosphoric acid group sandwiched by two nucleosides, namely, a phosphoric diester is extremely high. In other words, the zinc complex has a low coordinatability to a phosphoric diester moiety.

Further, the document, Hidekazu ARII, et al., [A novel diiron complex as a functional model for hemerythrin]. Journal of Inorganic Biochemistry, 82, pp. 153–162 (2000), recites an iron complex having a structure analogous to the structure of the zinc complex. The iron complex, however, is a product synthesized as a model of hemerythrin, namely, a carrier protein carrying oxygen molecules. As is the case with the above mentioned document, this document neither discloses nor remotely suggests coordinate bond of the iron complex to a phosphoric monoester moiety.

BRIEF SUMMARY OF THE INVENTION

In view of the above, it is an object of the present invention to overcome the problems residing in the prior art. It is another object of the present invention to provide a method for labeling phosphorylated peptides, namely, proteins, for easy detection, and a method for selectively adsorbing the phosphorylated peptides for purification or the like.

It is still another object of the present invention to provide compounds that are capable of being highly coordinated to the phosphorylated peptides and usable in the labeling method and the selective adsorbing method, a process for producing the compounds, and raw material compounds usable in the production process.

According to an aspect of the present invention, provided is a method for labeling a phosphorylated peptide by a complex compound represented by the formula (I):

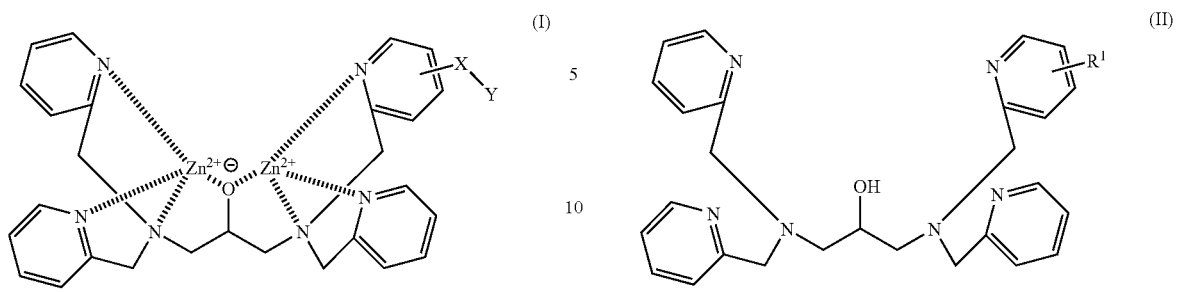

wherein X is a linker moiety, and Y is a labeling group.

According to another aspect of the present invention, provided is a method for selectively adsorbing a phosphorylated peptide by using the above complex compound.

According to yet another aspect of the present invention, provided is the above complex compound.

According to still another aspect of the present invention, provided is a process for producing the compound (I), comprising Scheme 1.

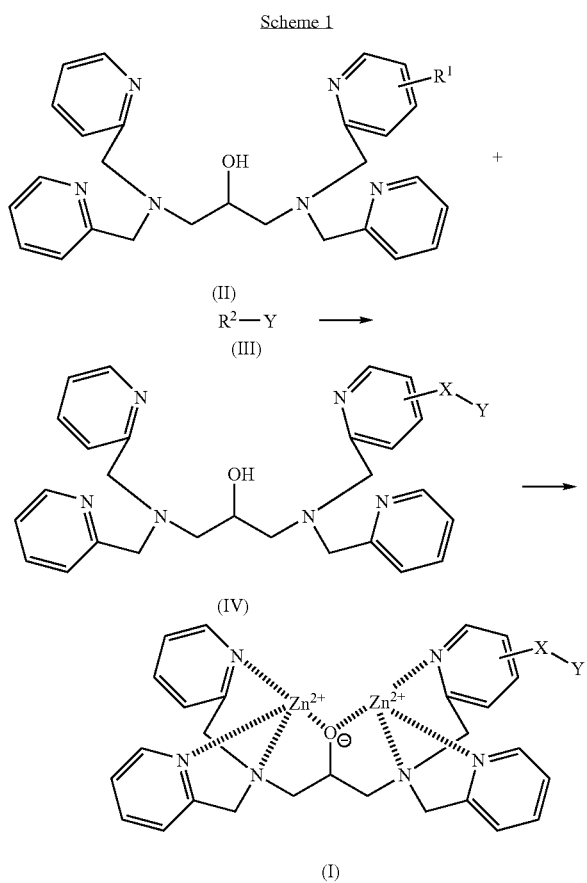

wherein $R^1$ and $R^2$ each is a reactive group for forming the linker moiety X, and Y is a labeling group.

According to still another aspect of the present invention, provided is a compound represented by the formula (II):

wherein $R^1$ is a reactive group except an aminomethyl group, a hydroxymethyl group, an amino group, and a carboxyl group.

According to the inventive labeling method, the phosphorylated peptide, namely, a protein can be easily detected. Thus, the present invention is useful in diagnosing diseases or the like with use of samples derived from living organisms or the like.

Further, since the inventive compound (I) shows a unique coordination bond to the two hydroxy groups in a phosphoric monoester moiety or phosphoric ion, the inventive compound (I) is useful as a compound usable in the inventive method. Additionally, the inventive compound (I) is useful for purifying or concentrating phosphorylated peptide and obtaining the chemical information of phosphorylated peptide.

These and other objects, features and advantages of the present invention will become more apparent upon reading of the following detailed description along with the accompanying drawings.

BRIEF DESCRIPTION OF THE DRAWINGS

FIG. 2 is an illustration showing electrophoresis gels, which is dyed by the inventive zinc complex (A) and further conventional dye (B). This illustration makes it clear that the inventive method can identify only phosphorylated peptide, while conventional method dyes all of the peptide.

FIG. 9 is an illustration showing electrophoresis gels, which is dyed by the inventive zinc complex (A) and further conventional dye (B). This illustration makes it clear that the inventive method can identify only phosphorylated peptide, while conventional method dyes all of the peptide.

DETAILED DESCRIPTION OF THE INVENTION

Figure 1:
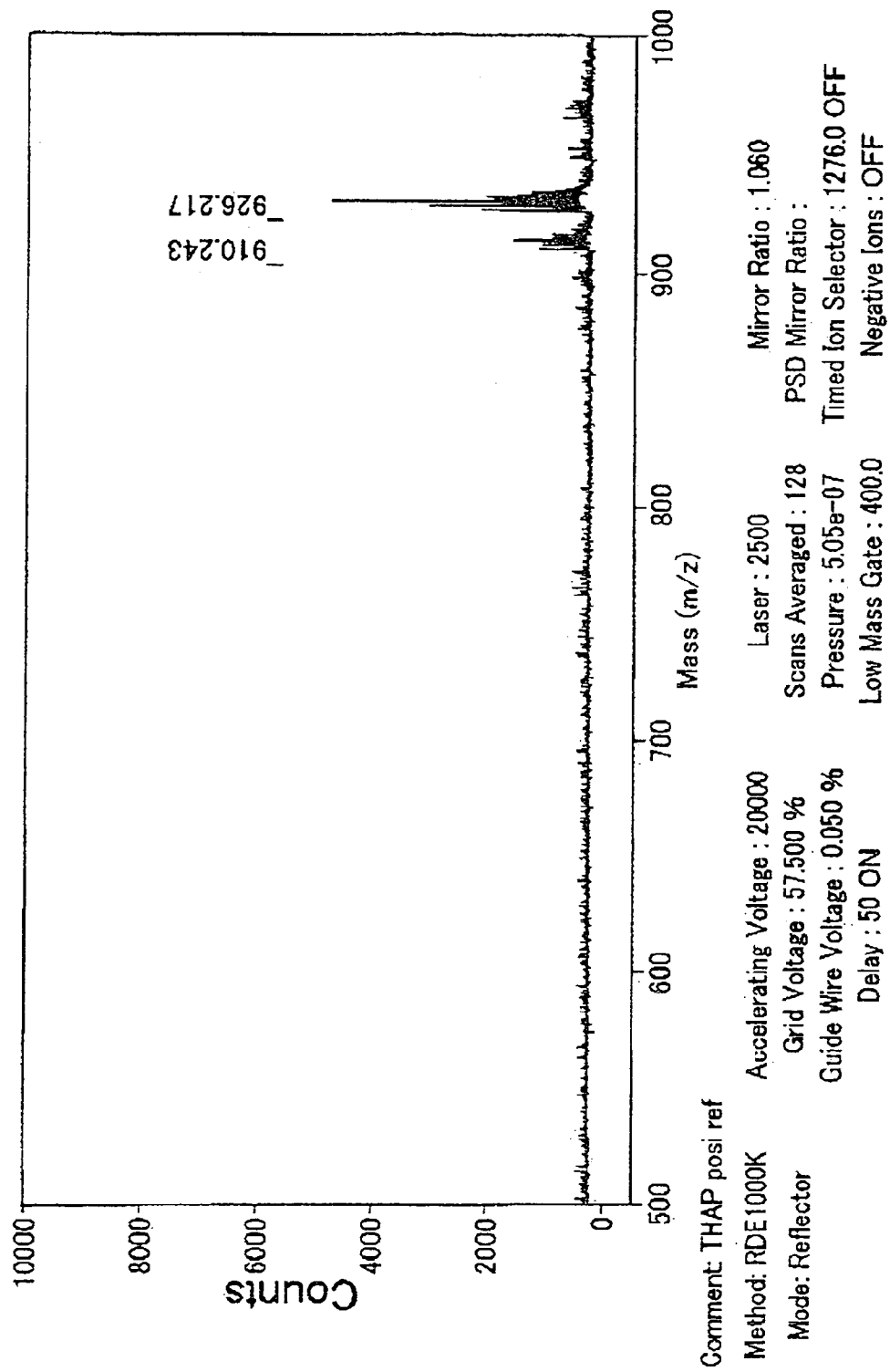
FIG. 1 is an illustration showing a result of examination by an MALDI-TOF mass spectrometer regarding a zinc complex according to the present invention.

A primary feature of the inventive method resides in that a phosphorylated peptide can be easily identified by forming a composite compound in which a complex compound having a labeling group as represented by the formula (I) is specifically bonded to the phosphorylated peptide.

There have been known various metallic complexes capable of being bonded to a phosphoric acid group. However, a compound which is analogous to the compound represented by the formula (I) and has a labeling group has been unknown. The inventors found that use of the complex compound represented by the formula (I) is advantageous in easily detecting and identifying a phosphorylated peptide even in a sample of a living organism containing a multitude of kinds of peptides, and accomplished the present invention.

In the following, a method for labeling phosphorylated peptides according to an embodiment of the present invention is described First, prepared is a sample containing substantially all the possible kinds of peptides constituting a tissue cell to be examined. The preparation can be conducted according to a conventional method practiced in the biochemistry.

Next, the peptides contained in the sample are separated. The separation method is not specifically limited, and a conventional separation method such as electrophoresis can be applied.

In case of implementing the electrophoresis, the gel after the electrophoresis is immersed in a solution containing the complex compound represented by the formula (I) to label the phosphorylated peptide, and then, the phosphorylated peptide is detected by a detecting method depending on the kind of the labeling group.

A solvent usable in the solution containing the complex compound represented by the formula (I) is not specifically limited, as far as the solvent does not hinder detection of the phosphorylated peptide. Water including a buffer and a solution containing a salt other than a buffer; alcohols such as methanol and ethanol; and a mixed solvent containing these components are examples of the solvent. Preferably, an aqueous solvent is used primarily for the purpose of preventing denaturation of the peptide.

Next, the compound (I) used in the above method is described.

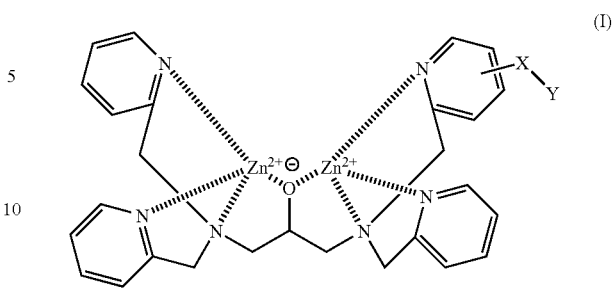

wherein X is a linker moiety, and Y is a labeling group.

In the formula (I), Zn is selected as a coordinate metal because Zn is highly coordinated to a phosphoric acid group in a phosphorylated protein. namely, a phosphoric monoester moiety.

The linker moiety in the present specification and the claims means a group capable of linking a main skeleton and a labeling group. The linker moiety facilitates production of the compound (I), and inhibits the labeling group from hindering coordination of the compound (I) to the phosphoric acid group bonded to the peptide. In view of this, the linker moiety may be a coordination bond which directly links the main skeleton and the labeling group if it is easy to obtain a raw material compound in which a labeling group is directly linked to a main skeleton in synthesizing the compound (I), or if the labeling group is of such a small size that hindrance of coordination of the compound (I) to the phosphoric acid group is securely prevented.

The kind of the linker moiety in the present specification and the claims is not specifically limited, as far as the linker moiety has the above functions. Examples of the linker moiety are: a C1-C6 alkylene group, an amino group (—NH—), an ether group (—O—), a thioether group (—S—), a carbonyl group (—C(=O)—), a thionyl group (—C(=S)—), an ester group, an amide group, a urea group (—NHC(=O)NH—), a thiourea group (—NHC(=S)NH—); a C1–C6 alkylene group having, at one end thereof, a group selected from the group consisting of an amino group, an ether group, a thioether group, a carbonyl group, a thionyl group, an ester group, an amide group, a urea group, and a thiourea group; a C1–C6 alkylene group having, at the opposite ends thereof, two groups selected from the group consisting of an amino group, an ether group, a thioether group, a carbonyl group, a thionyl group, an ester group, an amide group, a urea group, and a thiourea group, wherein the groups at the opposite ends are identical to or different from each other; and a group in which two or more than two groups selected from the group consisting of an amino group, an ether group, a thioether group, a carbonyl group, a thionyl group, an ester group, an amide group, a urea group, a thiourea group, and a C1–C6 alkylene group are linearly linked.

The C1–C6 alkylene group means a bivalent aliphathic hydrocarbon group having 1 to 6 carbon atoms of a straight chain or a branched chain, such as methylene, ethylene, propylene, tetramethylene, hexamethylene, methylethylene, methylpropylene, and dimethylpropylene, and preferably is a C1–C4 alkylene group, and more preferably is a C1–C2 alkylene group.

The labeling group in the present specification and the claims is not specifically limited, as far as it is generally used in the biochemistry. However, a compound containing a radioisotope is not preferable in the aspect of handling. Examples of the labeling group are a fluorescent group, a group containing a nitro oxide radical and biotin.

The fluorescent group is a substituent capable of stably generating fluorescence of a relatively long wavelength, and a group generally used in the biochemistry can be unlimitedly used as the fluorescent group, irrespective of the property that the compound is soluble in water or oil. Examples of the fluorescent group are aminomethylcoumarin and its derivatives, fluoroscein and its derivatives, tetramethylrhodamine and its derivatives, anthraniloyl and its derivatives, nitrobenzoxadiazole and its derivatives, and dimethylaminonaphthalene and its derivatives.

The group containing a nitro oxide radical is a group having a stable radical, and is capable of detecting a phosphorylated peptide by electron spin resonance (ESR). Generally, a biological molecule does not show electron spin resonance because it does not have an unpaired electron. On the other hand, since a peptide bonded by the compound (I) having a nitro oxide radical being coordinated thereto shows electron spin resonance, the phosphorylated peptide is identifiable.

Biotin has specific and high affinity to avidin derived from albumen and streptoavidin derived from actinomycetes. In view of this, the inventive complex compound can be specifically bonded to an enzyme by way of biotin and avidin or streptoavidin, by bonding avidin or streptoavidin to the inventive compound (I) having biotin as a labeling group and further bonding a biotinated enzyme. The phosphorylated peptide can be identified by using the enzyme such as alkaliphosphotase, peroxidase and luciferase, and by using a coloring reagent depending on the kind of the enzyme. For instance, if first phosphorylated peptide is bonded by the inventive complex compound, then the complex compound is bonded by alkaliphosphotase as the enzyme via streptoavidin, further nitro blue tetrazolium and 5-bromo-4-chloro-3-indolyl phosphate as the coloring reagents are added, and the mixture is reacted for several hours, the phosphorylated peptide turns into purple, thereby making it possible to identify the phosphorylated peptide. Further, streptoavdin labeled with a fluorescent pigment such as rhodamine is commercially available. Use of the streptoavidin labeled with the fluorescent pigment makes it possible to identify a phosphorylated peptide by a known fluorescent image analyzing method.

Next, a method for selectively adsorbing phosphorylated peptides according to an embodiment of the present invention is described.

According to the method for selectively adsorbing phosphorylated peptides, biotin or the like capable of specifically being bonded to a specific compound is used as a labeling group. For instance, an agarose gel with streptoavidin being bonded thereto is commercially available. An agarose gel with the inventive complex compound being bonded thereto can be obtained by applying the inventive complex compound having biotin as a labeling group to an agarose gel for reaction. The phosphorylated peptide in a mixed sample can be selectively adsorbed to the inventive complex compound by applying the mixed sample to the agarose gel. After the selective adsorption, adding a phosphoric acid buffer or the like capable of desorbing the phosphorylated peptide from the inventive complex compound makes it possible to obtain the phosphorylated peptide exclusively In this way, using the agarose gel is advantageous in purifying or concentrating a phosphorylated peptide without electrophoresis. Also, magnetic beads with streptoavidin being bonded thereto are commercially available. Use of the magnetic beads also makes it possible to purify or concentrate a phosphorylated peptide. Further, plates with streptoavidin being bonded thereto are commercially available for measuring surface plasmon resonance (SPR). A plate with the inventive complex compound being bonded thereto for measuring surface plasmon resonance can be obtained by applying the inventive complex compound having biotin as a labeling group onto the plate. Presence or absence of the phosphorylated peptide in a sample can be detected by measuring the surface plasmon resonance (SPR) of the plate.

It is possible to synthesize a compound equivalent to the compound (I), in which a methyl group or the like is introduced to a pyridine ring, to provide substantially the same operations and effects as in the embodiment of the present invention. Such a compound equivalent to the compound (I) is embraced in the scope of the present invention.

The location of the (—X—Y) group in the inventive compound is not specifically limited. The (—X—Y) group may be located at the site as shown in the compound (I').

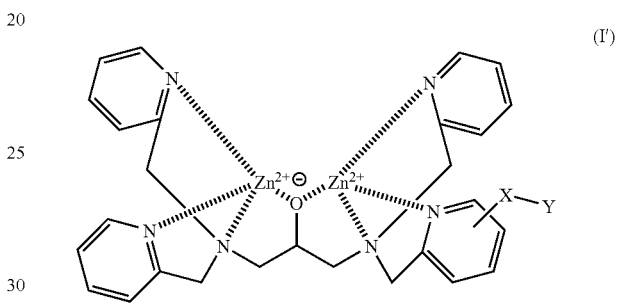

(I')

The compound (I) and the compound (I') are substantially equivalent to each other. Although it is not clear as to which compound is synthesized, the compound (I) or the compound (I'), what is actually synthesized is conceivably a synthesized mixture of the compound (I) and the compound (I'). It is needless to say that the compound (I') is embraced in the scope of the present invention.

A complex compound represented by the formula (I) can be easily produced by a process comprising Scheme 1.

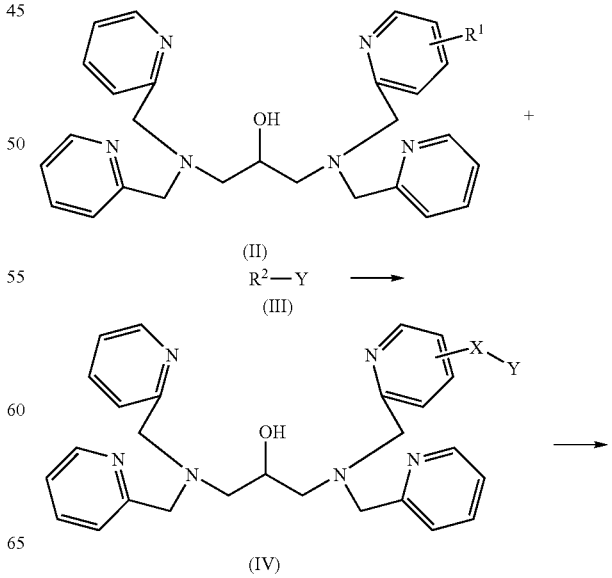

Scheme 1

-continued

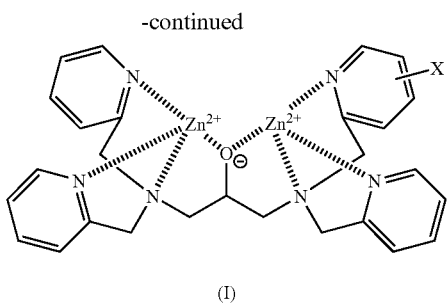

(I)

wherein X and Y is the same as defined above, and $R^1$ and $R^2$ each is a reactive group for forming the linker moiety X.

In the above Scheme, the labeling group Y is introduced to the main skeleton via the linker moiety X by reacting the reactive groups $R^1$ and $R^2$.

The kind of $R^1$, $R^2$, the solvent, a reaction temperature, a reagent other than the above, a purification method, and other factors are primarily determined by the kind of X. For instance, in case of introducing a labeling group via an amino group (a secondary or tertiary amino group), as a combination of $R^1$ and $R^2$, a combination of a group having an amino group (a primary or a secondary amino group) at a distal end thereof and a elimination group such as a halogen atom. Condensing $R^1$ and $R^2$ under the presence of basic groups in the solvent is an example of general reaction condition. In case that $R^1$ is an active group, it is very easy to introduce a labeling group.

Next, the compound (I) can be synthesized by adding a metallic salt to a solution containing the compound (IV). Zinc (II) nitrate or zinc (II) acetate may be added as the metallic salt. In case that zinc (II) acetate is added, a compound represented by the following formula (V) in which acetic acid is temporarily coordinated is produced.

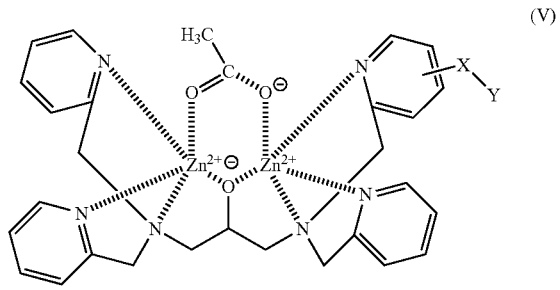

(V)

The compound (V) is chemically more stable than the compound (I), and accordingly useful in storage. The compound (V) is equivalent to the compound (I), and is usable in the similar manner as the compound (I). Specifically, by adding the compound (V) to the mixture containing the peptide, the phosphorylated peptide can be detected because the phosphoric monoester moiety is interchangeably coordinated to the compound (I) in place of the acetic acid.

The compound (II), namely, a raw material compound of the compound (I) can be synthesized by the following Scheme 2.

Scheme 2

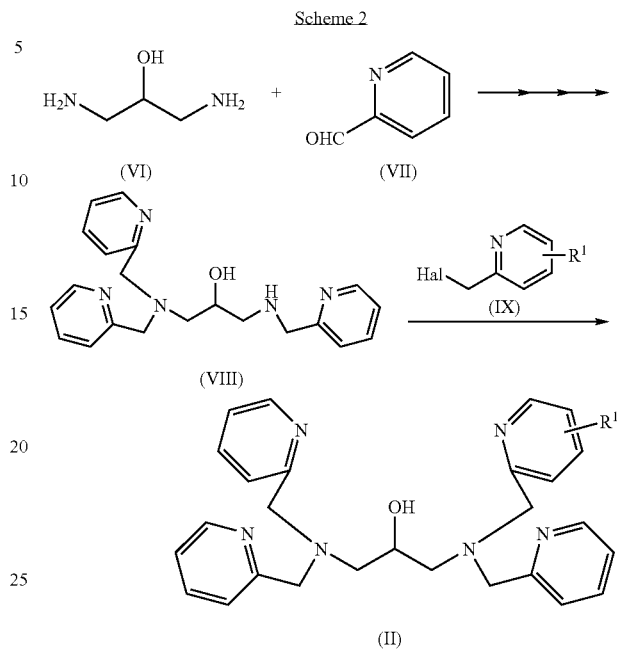

wherein $R^1$ is the same as defined above, and "Hal" is a halogen atom, and preferably is a bromine.

The compound (VI), i.e., 1,3-diamino-2-propanol, as a raw material compound may be commercially available. Further, since both the compound (VII) and the compound (IX) have a relatively simple structure, the compound (VII) and (IX) may be commercially available, or can be synthesized by a well-known method for a person skilled in the art.

In Scheme 2, first, the compound (VI) and the compound (VII) are reacted with each other under the presence of a catalyst for condensation to yield the compound (VIII). This reaction may be implemented step by step by introducing the compound (VII). Alternatively, the compound (VIII) can be obtained by a single step by using 3 or more equivalents of the compound (VII) to the compound (VI).

In Scheme 2, reductive amination is carried out as a condensation reaction. A solvent used in the reductive amination is not specifically limited, as far as the solvent is capable of substantially dissolving the compound (VI) and the compound (VII), and does not inhibit the amination. For instance, alcohols such as methanol, ethanol and isopropanol; ethers such as diethyl ether, tetrahydrofuran and dioxane; water; or a mixed solvent containing two or more of these components can be used as the solvent.

The reductive amination can be carried out with use of a conventional reducing reagent after condensing the compound (VI) and the compound (VII) under the presence of concentrated hydrochloric acid, as a catalyst.

An optimal condition regarding the reaction temperature and the reaction time can be optionally selected depending on the kind of the raw material compound or other factors. For example, the reaction may be carried out at a reaction temperature from 20 to 80° C. for a reaction time from 12 to 100 hours.

After the reaction is completed, the solvent and the like are distilled off under depressurization before adding water. After water is added, the resultant mixture is extracted with a water-insoluble solvent, and the organic layer is dried over anhydrous magnesium sulfate or the like. Thereafter, the solvent is distilled off under depressurization. Subsequently, the residue is purified by a well known process such as silica gel column chromatography, thereby to yield the compound (VIII).

The process for yielding the compound (VIII) is not limited to the process as shown by Scheme 2. Alternatively, the compound (VIII) may be synthesized using the compound (VI) and a halogen compound, for example.

Next, the compound (II) can be synthesized by reacting the compound (VIII) with the compound (IX). This reaction can be carried out by a know process of synthesizing tertiary amines. For instances the compound (VIII) and the compound (IX) are condensed under the presence of base in a solvent. In the condensing step, a protective group may be introduced and cleaved depending on the kind of $R^1$ according to needs. Alternatively, the compound (II) may be synthesized by implementing the condensing step with use of a compound having an inactive substituent group in place of using $R^1$ in the compound (IX), and by substituting $R^1$ for the inactive substituent group by functional group conversion. For instance, the condensing step is implemented by using a compound having a nitro group as the inactive substituent group and by substituting an amino group as the reactive group for the nitro group.

The following complex compound (X) can be used as a compound usable in the inventive method, in place of the complex compound (I).

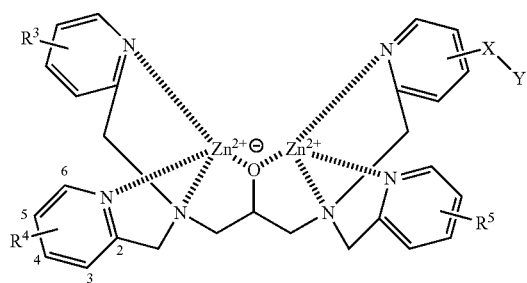

(X)

wherein X, Y is the same as defined above, and $R^3$ through $R^5$ each is an electron donating substituent group at the 4 or 6 position on the pyridine ring.

The complex compound (X) used in the inventive method is electrically enriched with pyridine nitrogen by the electron donating substituent group that has been introduced to an appropriate position for substitution. Accordingly, the complex compound (X) used in the inventive method is highly coordinated to zinc, thereby, making it possible to produce the complex compound (X) easily, while providing stability.

A manner of using the complex compound (X), a process for producing the complex compound (X), and a raw material compound for the complex compound (X) are substantially the same as those regarding the complex compound (I).

In the above methods and compound (I), it is preferable to use biotin, as the labeling group, in producing the complex compound. Use of biotin is preferred because biotin is easy to be handled, and has high usability in the point that it exhibits various colorings reactions. Use of biotin is effective in easily identifying the phosphorylated peptide.

In the following, production examples and experiment examples are illustrated to describe the present invention in detail. The present invention is, however, not limited to the illustrated examples.

EXAMPLES

Production Example 1-1

Methyl 6-bromomethylnicotinate

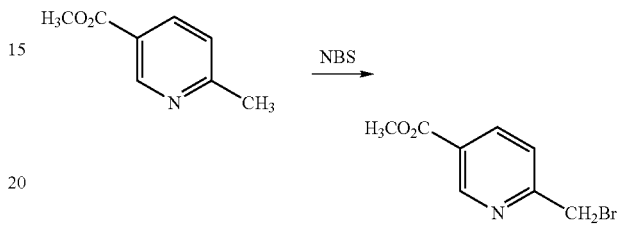

To a solution of methyl 6-methylnicotinate (50 g, 331 mmol) in carbon tetrachloride (625 mL), was added N-bromosuccinimide (59 g, 331 mmol). Further 1.0 g of benzoyl peroxide was added, the mixture was reacted at a temperature from 40 to 50° C. for 24 hours with irradiation of light from a projector.

After the reaction mixture was cooled, the precipitated crystals were separated by filtration. The filtrate was washed with an aqueous solution containing sodium hydrogencarbonate, and concentrated. The residue obtained by the concentration was purified by silica gel column chromatography, thereby to yield 37 g of the target compound. $^1$H-NMR (CDCl$_3$, 300 MHz): δ 3.96(3H, s, OCH$_3$), 4.58(2H, s, CH$_2$Br), 7.54(1H, d, Py), 8.30(1H, dd, Py), 9.17(1H, d, Py)

Production Example 1-2

N,N,N'-Tri(2-pyridylmethyl)-1,3-diaminopropane-2-ol

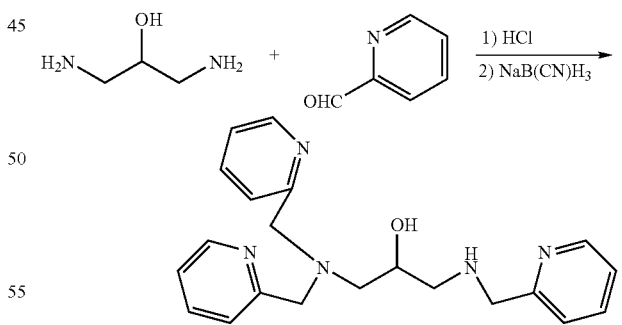

To a solution of 1,3-diaminopropane-2-ol (32.6 g, 362 mmol) in methanol (2400 mL), was added 60 mL of concentrated hydrochloric acid. Further 2-pyridine aldehyde (116.3 g, 1.09 mol) was added dropwise, and then sodium cyanoborohydride (50.16 g, 798 mmol) was added. After the addition was completed, the mixture was reacted at temperature for 3 days.

After concentrated hydrochloric acid was added to the solution and the pH of the solution was adjusted to 6, the resulting solution was concentrated to some extent. Then, 0.1N aqueous solution of sodium hydroxide was added to adjust the pH of the solution to 7, followed by extraction with chloroform. The extracts were collected and dried, the resultant was concentrated. The residue obtained by the concentration was purified by silica gel column chromatography, thereby to yield 34 g of the target compound.

$^1$H-NMR (CDCl$_3$, 300 MHz): δ 2.59–2.83(4H, m, CH$_2$), 3.86–4.01(7H, m, NCH$_2$Py, CH), 7.15(3H, dd, Py), 7.23–7.32(3H, m, Py), 7.56–7.65(3H, m, Py), 8.53(3H, dd, Py)

Production Example 1-3

N,N,N,'-Tri(2-pyridylmethyl)-N'-(5-methoxycarbonyl-2-pyridylmethyl)-1,3-diaminopropane-2-ol

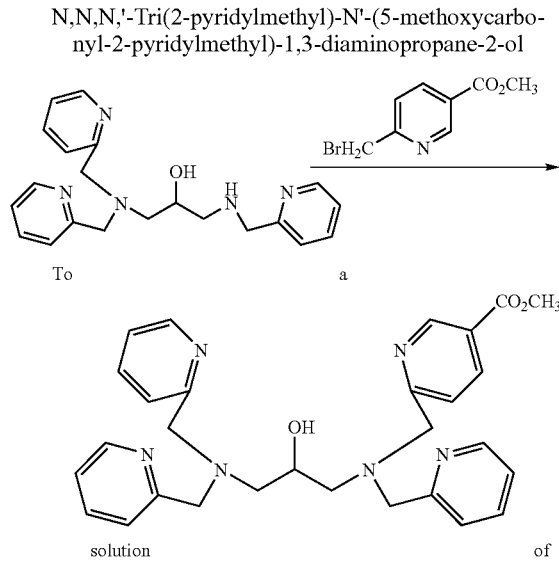

To a solution of N,N,N'-tri(2-pyridylmethyl)-1,3-diaminopropane-2-ol (18.2 g, 50 mmol) obtained in Production Example 1-2 in dried dimethylformamide (150 mL), was added potassium carbonate (13.8 g, 100 mmol), followed by addition of a solution of the methyl 6-bromomethylnicotinate (11.5 g, 50 mmol) obtained in Production Example 1-1 in dried dimethylformamide (75 mL) dropwise. After the dropwise addition was completed, the mixture was reacted at 50° C. for 1 hour.

After the reaction was completed, the solution was cooled. Then, the cooled solution was poured into 750 mL of water, and the pH of the solution was adjusted to 8 by adding 1N hydrochloric acid. After extraction with ethyl acetate, the extracts were collected, washed with water and brine, and concentrated. The residue obtained by the concentration was purified by silica gel column chromatography, thereby to yield 21.5 g of the target compound.

$^1$H-NMR (CDCl$_3$, 300 MHz);δ 2.58–2.73(4H, m, CH$_2$), 3.83–3.95(12H, m, OCH$_3$, NCH$_2$Py, CH), 7.10–7.14(3H, m, Py), 7.34 (3H, d, Py), 7.50–4.60(4H, m, Py), 8.17(1H, dd, Py), 8.50(3H, d, Py), 9.09(1H, d, Py)

Production Example 1-4

N,N,N'-Tri(2-pyridylmethyl)-N'-[5-N'''-(2-aminoethyl)carbamoyl-2-pyridylmethyl]-1,3-diaminopropane-2-ol

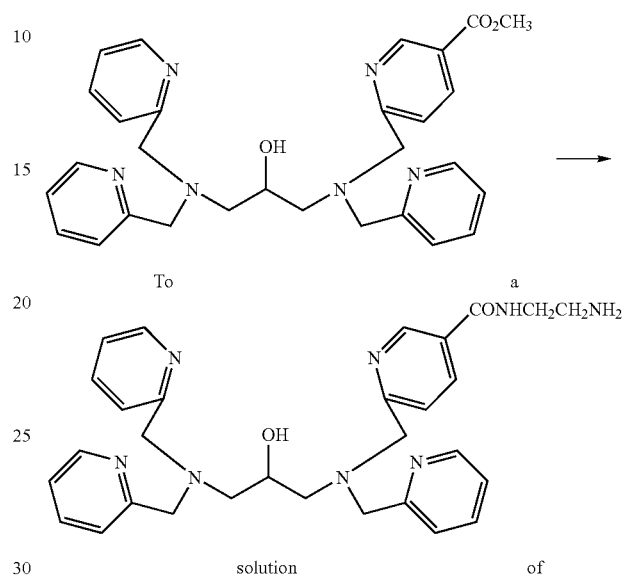

To a solution of N,N,N'-tri(2-pyridylmethyl)-N'-(5-methoxycarbonyl-2-pyridylmethyl)-1,3-diaminopropane-2-ol (9.7 g, 18.9 mmol) obtained in Production Example 1-3 in methanol (100 mL), was added ethylenediamine (22.7 g, 378 mmol) dropwise. After the dropwise addition, the mixture was reacted at room temperature for 3 days.

After the reaction was completed, the solution was concentrated, and the residue obtained by the concentration was purified by silica gel column chromatography, thereby to yield 9.72 g of the target compound.

$^1$H-NMR (CDCl$_3$, 300 MHz): δ 2.54–2.71(4H, m, CH$_2$), 2.94(2H, t, CH$_2$N), 3.49(2H, dt, CH$_2$N), 3.80–3.99(9H, m, NCH$_2$Py, CH), 7.12(3H, ddd, Py), 7.35(3H, d, Py), 7.45(1H, d, Py), 7.58(3H, ddd, Py), 8.02(1H, dd, Py), 8.49(3H, ddd, Py), 8.89(1H, d, Py)

Production Example 1-5

N,N,N'-Tri(2-pyridylmethyl)-N'-[5-N'''-(7-nitro-2,1,3-benzoxadiazole-4-ylaminoethyl)carbamoyl-2-pyridylmethyl]-1,3-diaminopropane-2-ol

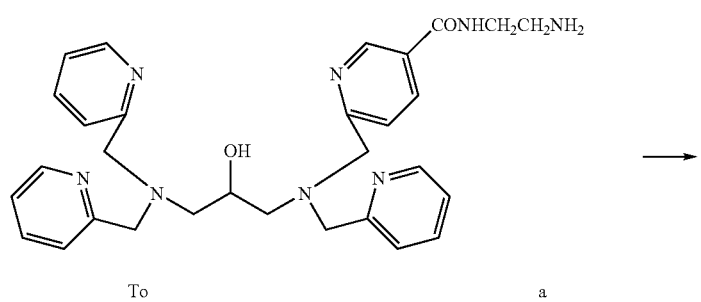

To a

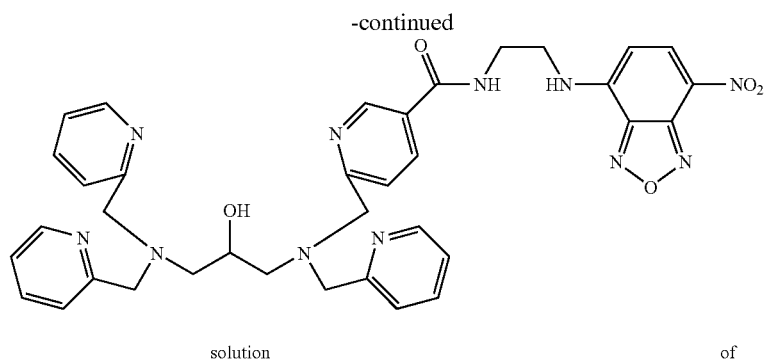

solution of N,N,N'-tri(2-pyridylmethyl)-N'-[5-N''-(2-aminoethyl)carbamoyl-2-pyridylmethyl]-1,3-diaminopropane-2-ol (200 mg, 0.37 mmol) obtained in Production Example 1-4 in acetonitrile (20 mL), was added sodium hydrogencarbonate (336 mg, 4.0 mmol), followed by addition of 4-chloro-7-nitro-2,1,3-benzoxadiazole (73.8 mg, 0.37 mmol). The mixture was reacted at room temperature for 2 hours.

After the reaction was completed, the solution was concentrated. Then, 50 mL of dichloromethane and 50 mL of water were added, and the organic layer and aqueous layer were separated. The organic layer was dried over anhydrous sodium sulfate, concentrated, and the obtained residue was purified by silica gel column chromatography, thereby to yield 71.2 mg of the target compound.

$^1$H-NMR (CDCl$_3$, 300 MHz): δ 2.46–2.69(4H, m, CH$_2$), 3.65–3.95(13H, m, NCH$_2$CH$_2$N, NCH$_2$Py, CH), 6.06(1H, d, Ar), 7.08–7.13(3H, m, Py), 7.32(3H, d, Py), 7.42(1H, d, Py), 7.56(3H, ddd, Py), 7.96(1H, dd, Py), 8.44–8.48(3H, m, Py), 8.19(1H, d, Ar), 8.83(1H, d, Py)

Production Example 1-6

Solution Containing the Inventive Zinc Complex

Prepared was 50 μM aqueous solution containing the compound obtained in Production Example 1-5, followed by addition of zinc nitrate of 2 equivalents to the solution. Thus, a solution containing the inventive zinc complex was prepared.

The zinc complex was identified according to the following method. Specifically, the compound obtained in Production Example 1-5 was dissolved in a phosphoric acid buffer (pH=6.86) to obtain the 50 μM solution, followed by addition of zinc nitrate of 2 equivalents to the solution. The inventive zinc complex in the solution exhibits the following structure, and was identified by MALDI-TOF mass spectrometer (Matrix: 2',4',6'-trihydroxyacetophenone, Mode: reflector, Accelerating Voltage: 20000V, Grid Voltage: 57.500%, Laser: 2500, Scans Averaged: 128, Pressure: 5.05e-07).

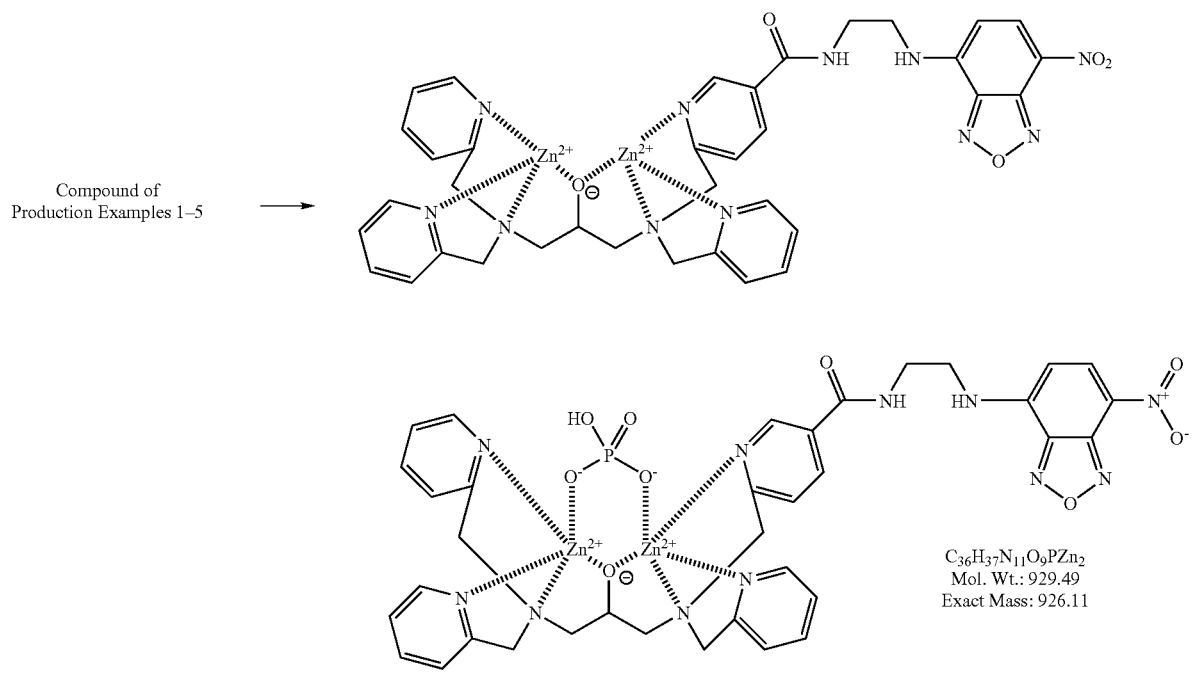

Compound of Production Examples 1–5 →

C$_{36}$H$_{37}$N$_{11}$O$_9$PZn$_2$
Mol. Wt.: 929.49
Exact Mass: 926.11

The result of measurement by the MALDI-TOF mass spectrometer is shown in FIG. 1. As shown in FIG. 1, a molecular ion peak at 926.2 (exact mass: 926.11) was observed. It is considered that a molecular ion peak at 910.2 appeared because the oxygen in the oxadiazole group was eliminated.

Production Example 2-1

N,N,N'-Tri(2-pyridylmethyl)-N'-[5-N'''-(2-D-biotinamidoethyl)carbamoyl-2-pyridylmethyl]-1,3-diaminopropane-2-ol

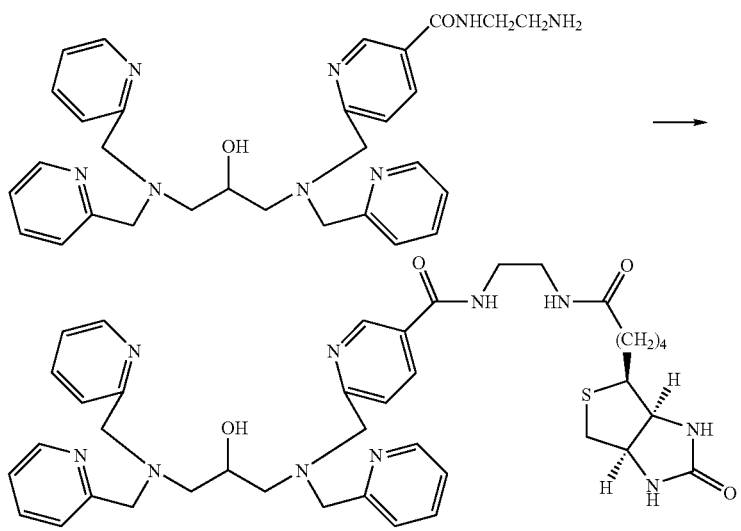

To a solution of D-biotin (137 mg, 0.56 mmol) in dimethylformamide (10 mL), was added 1,1'-carbonyldiimidazole (116 mg, 0.72 mmol). The mixture was reacted at room temperature for 12 hours. Thereafter, the solution was cooled with ice, followed by dropwise addition of a solution of N,N,N'-tri(2-pyridylmethyl)-N'-[5-N'''-(2-aminoethyl)carbamoyl-2-pyridylmethyl]-1,3-diaminopropane-2-ol (260 mg, 0.48 mmol) obtained in Production Example 1-4 in dimethylformamide (3 mL). The cooling bath was detached, and the reaction was carried out at room temperature for 2 hours.

After the reaction was completed, the solution was poured into 50 mL of water, followed by extraction with 50 mL of chloroform twice. After the extracts were concentrated, the crude product was purified by silica gel column chromatography, thereby to yield 265 mg of the target compound $^1$H-NMR (CDCl$_3$, 300 MHz): δ 1.27–1.47(2H, m, CH$_2$), 1.50–1.75(4H, m, CH$_2$), 2.13–2.26(2H, m, COCH$_2$), 2.52–2.74(5H, m, NCH$_2$, SCH$_2$), 2.79–2.88(1H, m, SCH$_2$), 3.01–3.12(1H, m, SCH), 3.43–3.65(4H, m, NCH$_2$CH$_2$N), 3.80–4.02(9H, m, NCH$_2$Py, CHO), 4.22–4.28(1H, m, NCH), 4.42–4.49(1H, m, NCH), 5.83(1H, bs, NHCO), 6.60(1H, bs, NHCO), 7.07–7.18(3H, m, Py), 7.31–7.38(3H, m, Py), 7.44(1H, d, Py), 7.59(3H, ddd, Py), 8.03(1H, dd, Py), 8.15(1H, bs, NHCO), 8.42–8.58(3H, m, Py), 8.94(1H, d, Py)

Production Example 2-2

Solution Containing the Inventive Zinc Complex

Compound of Production Examples 2–1 →

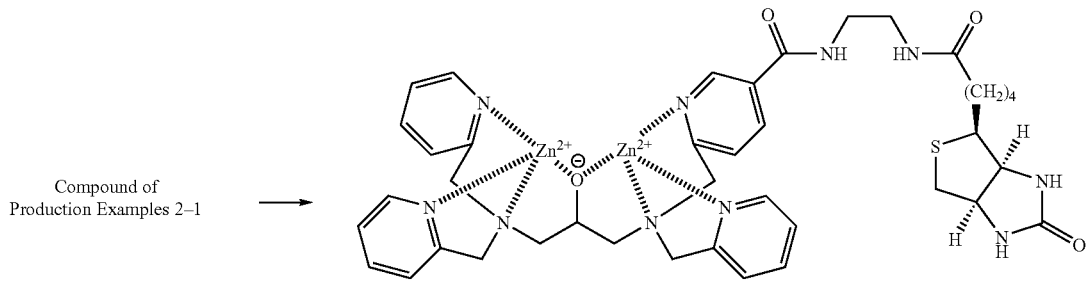

The compound obtained in Production Example 2-1 was dissolved in a phosphoric acid buffer (pH=6.86) to obtain 3 mM solution, followed by addition of zinc nitrate of 2 equivalents to the solution.

The inventive zinc complex in the solution exhibits the following chemical structure, and was identified by the MALDI-TOF mass spectrometer (Matrix: 2',4',6'-trihydroxyacetophenone).

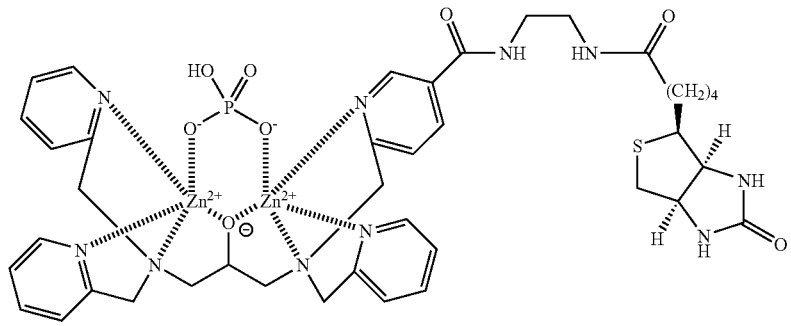

C₄₀H₅₀N₁₀O₈PSZn₂
Mol. Wt.: 992.69
Exact Mass: 989.19

Figure 3:
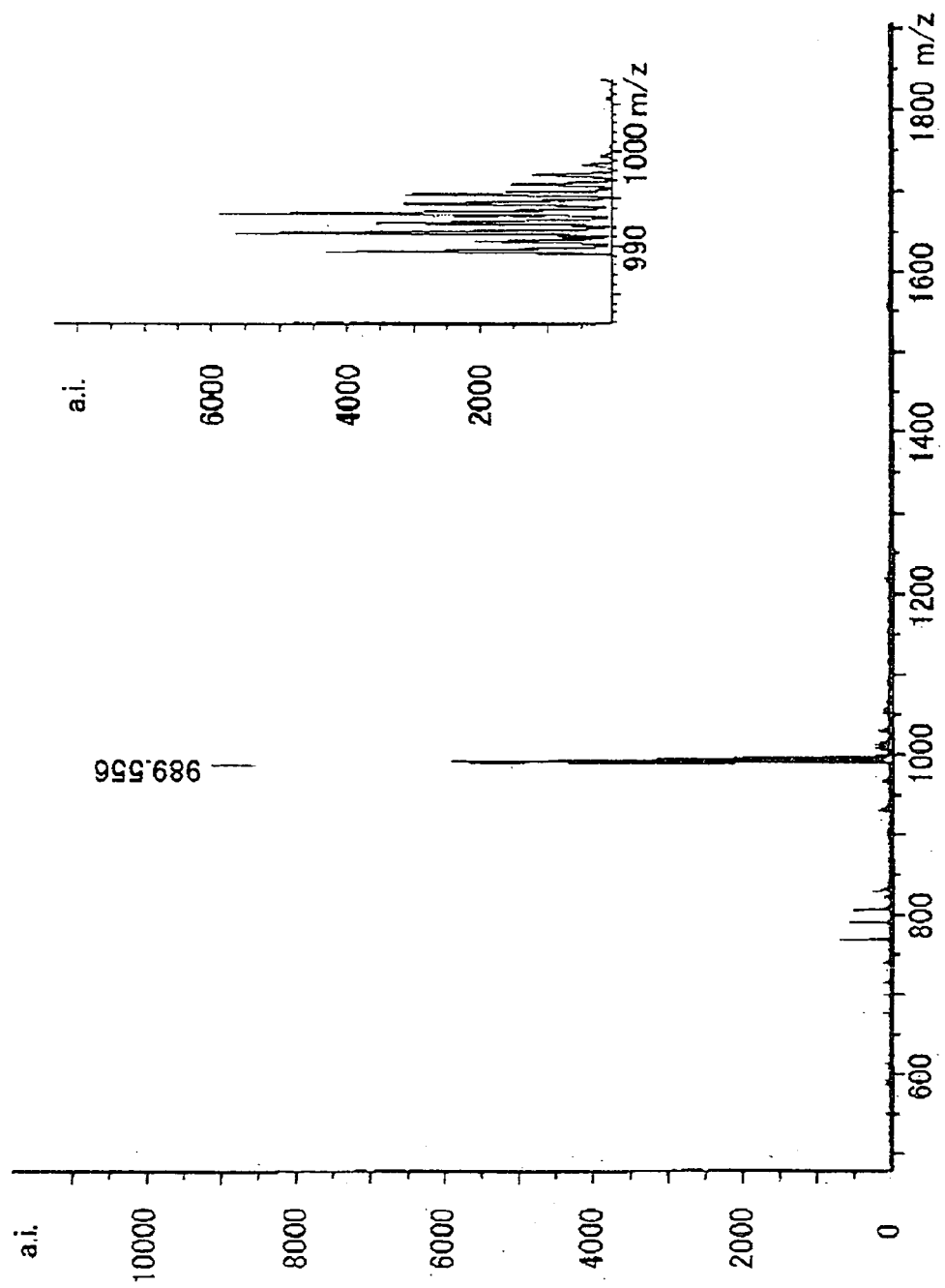
FIG. 3 is an illustration showing a result of examination by the MALDI-TOF mass spectrometer regarding a zinc complex according to the present invention, as well as an enlarged illustration showing a certain region of the examination result.

A result of measurement by the MALDI-TOF mass spectrometer is shown in FIG. 3. As shown in FIG. 3, a molecular ion peak at 989.6 (exact mass: 989.19) is observed.

Experimental Example 1

10% Native-polyacrylic Amide Gel Electrophoresis

First, prepared were gels for electrophoresis, a pH buffer for electrophoresis, and a coloring solution for dissolving samples under the following conditions.

Stacking gel;
    125 mM of Tris-hydrochloric acid buffer (pH=6.8)
    4.5% (w/v) of polyacrylamide (acrylamide:bisacrylamide=30:1)

Separation gel:
    375 mm of Tris-hydrochloric acid buffer (pH=8.8)
    10% (w/v) of polyacrylamide (acrylamide:bisacrylamide=30:1)

pH buffer for electrophoresis (pH=8.3):
    25 mM of Tris
    190 mM of glycine

Coloring solution for dissolving samples (3-times concentrated solution):
    195 mM of Tris-hydrochloric acid buffer (pH=6.8)
    10% (w/v) of glycerol
    0.1% (w/v) of bromo phenol blue (BPB), as a coloring marker used in electrophoresis Next, 2 μg each of 1: Bovine Serum Albumin, 2: β-casein (phosphorylated), and 3: β-casein (de-phosphorylated) was dissolved in the coloring solution to prepare samples. The respective samples were plotted on the gel. Then, a constant electric current of 4 mA was applied until the coloring marker was flowed out.

The gel was immersed in the zinc-complex-containing solution (50 μM) obtained in Production Example 1-6 for about 30 minutes. Then, the gel was taken out from the solution, and photographed under irradiation by a UV lamp. Further, the gel was dyed with Coomassie brilliant blue according to a conventional dying process, and the dyed gel was photographed. The gel dyed with the zinc-complex-containing solution is referred to as "gel A", and the gel dyed with Coomassie brilliant blue is referred to as "gel B", both of which are shown in FIG. 2.

As is obvious from FIG. 2, according to the inventive method, β-casein being bonded with phosphoric acid can be identified exclusively. Thus, it is clear that the inventive method is advantageous in identifying phosphorylated peptide exclusively in samples derived from living organisms.

Production Example 3-1

N,N,N'-Tri(2-pyridylmethyl)-N'-[5-N"-2-(6-D-biotinamidohexacarboxyamidoethyl)carbamoyl-2-pyridylmethyl]-1,3-diaminopropane-2-ol

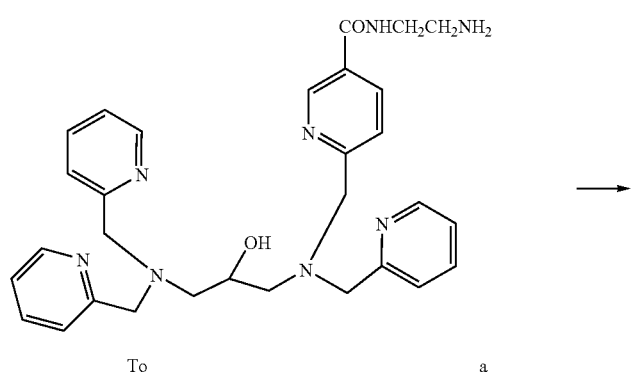

To                  a

-continued

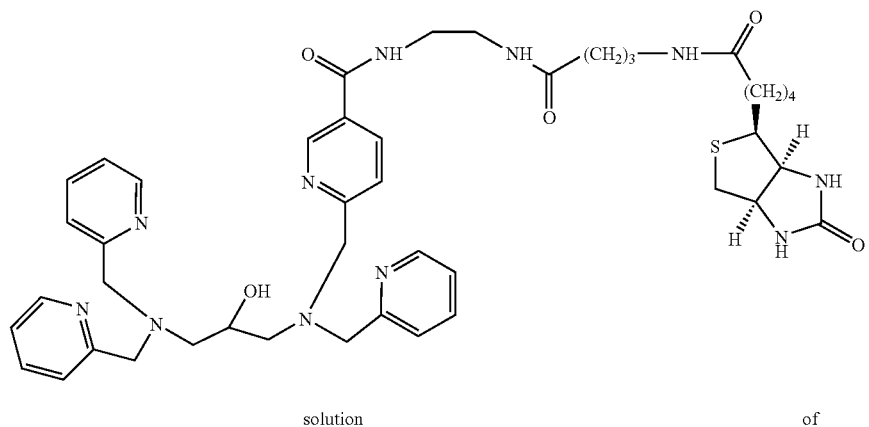

solution of N,N,N'-tri(2-pyridylmethyl)-N'-[5-N"-(2-aminoethyl)carbamoyl-2-pyridylmethyl]-1,3-diaminopropane-2-ol (113 mg, 0.21 mmol) obtained in Production Example 1-4 in acetonitrile (10 mL), was added a solution of 5-(N-succineimidyloxycarbonyl)pentyl-D-biotinamide (95 mg, 0.21 mmol) in dimethylsulfoxide (2 mL) dropwise.

After the mixture was reacted at room temperature for 6 hours, the reaction mixture was concentrated, and the crude product obtained by the concentration was purified by silica gel column chromatography, thereby to yield 136 mg of a target compound (yield: 76%).

$^1$H-NMR (CDCl$_3$, 500 MHz): δ 1.25–1.32(2H, m, CH$_2$), 1.38–1.47(4H, m, CH$_2$), 1.56–1.67(5H, m, CH$_2$), 1.68–1.77 (1H, m, CH$_2$), 2.11–2.22(4H, m, COCH$_2$), 2.58(2H, dd, J=8.0 and 13.3 Hz, NCH), 2.66(1H, dd, J=3.9 and 13.3 Hz, NCH), 2.68(1H, dd, J=3.9 and 13.3 Hz, NCH), 2.71(1H, dd, J=3.0 and 13.3 Hz, SCH), 2.88(1H, dd, J=5.2 and 13.0 Hz, SCH), 3.07–3.21(3H, m, NCH, SCH), 3.45–3.59(4H, m, NCH$_2$), 3.82–3.91(8H, m, NCH$_2$Py), 3.94(1H, tt, J=3.9 and 8.0 Hz, OCH), 4.28–4.32(1H, m, NCH), 4.46–4.50(1H, m, NCH), 5.62(1H, bs, NHCO), 6.40(1H, bs, NHCO), 6.62(1H, t, J=5.7 Hz, NHCO), 7.10–7.14(3H, m, Py), 7.23(1H, t, J=6.0 Hz, NHCO), 7.32–7.36(3H, m, Py), 7.43(1H, d, J=8.2 Hz, Py), 7.56–7.61(3H, m, Py), 8.06(1H, dd, J=2.3 and 8.2 Hz, Py), 8.17(1H, t, J=5.0 Hz, NHCO). 8.46–8.50(3H, m, Py), 8.96(1H, d, J=2.3 Hz, Py) $^{13}$C NMR (CDCl$_3$, 125 MHz): δ 25.0(CH$_2$), 25.5(CH$_2$), 26.2(CH$_2$), 27.7(CH$_2$), 27.8 (CH$_2$), 29.0(CH$_2$), 35.6(CH$_2$CO), 36.1(CH$_2$CO), 39.0 (CH$_2$NH), 39.3(CH$_2$NH), 40.7(CH$_2$S), 41.0(CH$_2$NH), 55.6 (CH$_2$S), 59.2(CH$_2$N), 60.2(CHNH), 60.7(CH$_2$Py), 60.8 (CH$_2$Py). 61.0(CH$_2$Py), 61.8(CHNH), 67.4(CHOH), 122.1 (Py), 122.8(Py), 123.2(Py), 128.5(Py), 135.6(Py), 136.5 (Py), 148.0(Py), 149.0(Py), 159.3(Py), 159.4(Py), 162.6 (Py), 163.9(NCON), 166.3(CONH), 173.4(CONH), 174.9 (CONH)

Production Example 3-2

Solution Containing the Inventive Zinc Complex

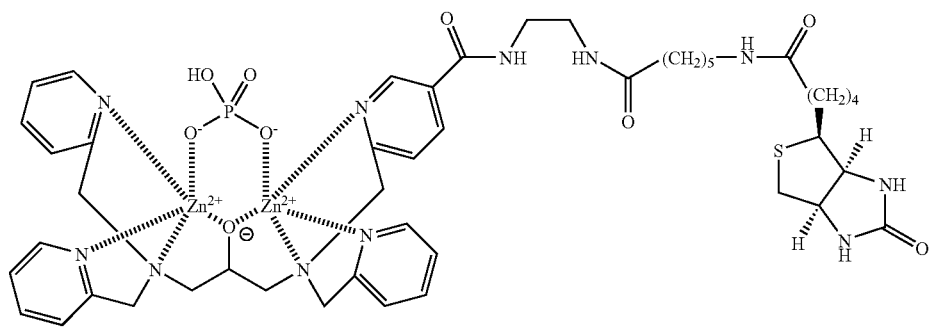

C$_{46}$H$_{61}$N$_{11}$O$_9$PSZn$_2$
Mol. Wt.: 1105.85
Exact Mass: 1102.27

To a phosphoric acid buffer (pH=6.86), dissolved was 200 nmol of the compound obtained in Production Example 3-1 to prepare 3 mM solution containing the compound, followed by addition of zinc nitrate of 2 equivalents to the solution. Thus, a solution containing the inventive zinc complex was prepared.

Figure 4:
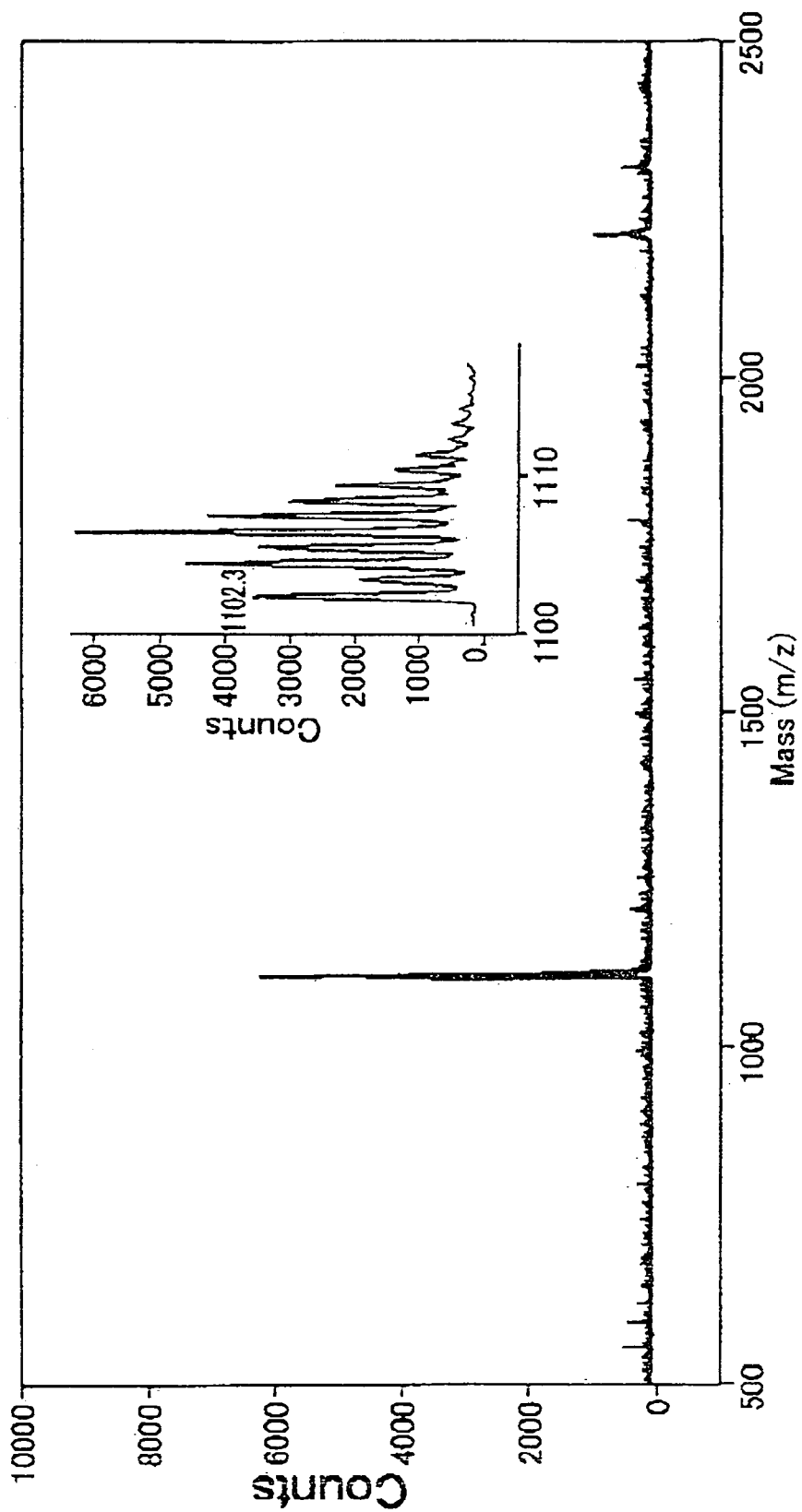
FIG. 4 is an illustration showing a result of examination by the MALDI-TOF mass spectrometer regarding a zinc complex according to the present invention, as well as an enlarged illustration showing a certain region of the examination result.

The solution was analyzed by the MALDI-TOF mass spectrometer (matrix: 2',4',6'-trihydroxyacetophenone), and the zinc complex was identified. A result of measurement by the MALDI-TOF mass spectrometer is shown in FIG. 4. As shown in FIG. 4, a molecular ion peak at 1102.3 (exact mass: 1102.27) was observed.

Experimental Example 2

The suspension (0.3 mL) containing Streptavidin agarose (quantity of the bonded moiety of biotin: 60 to 120 nmol/mL) and a buffer (Sigma-Aldrich Co.) was charged in a centrifugal filter unit (volume: 0.5 mL filter pore diameter: 0.22 μm). The filter unit was subjected to centrifugal separation at centrifugal acceleration of 2,000×g for 15 seconds, followed by filtration of the suspension. 5.0 mM Tris-acetate buffer (pH=7.4, 0.30 mL) was charged in the filter unit, then the filter unit was subjected to centrifugal separation at 2,000×g for 15 seconds and filtration for washing. This centrifugal separation and filtration step for washing was cyclically repeated for 5 times.

To the filter unit, charged was 5.0 mM Tris-acetate buffer (pH=7.4, 0.30 mL) dissolving 120 nmol/mL of the compound obtained in Production Example 3-1 and 500 nmol/mL of zinc acetate. The filter unit was brought to an equilibrium state for 5 minutes, and then, subjected to centrifugal separation at 2,000×g for 15 seconds and filtration. Next, 5.0 mM Tris-acetate buffer (pH=7.4, 0.30 mL) was charged in the filter unit, and subjected to centrifugal separation at 2,000×g for 15 seconds and filtration for washing. This centrifugal separation and filtration step for washing was cyclically repeated for 5 times. Further, 5.0 mM Tris-acetate buffer (pH=7.4, 0.30 mL) dissolving 10 nmol/mL of zinc acetate was charged in the filter unit, and subjected to centrifugal separation at 2,000×g for 15 seconds and filtration for washing. This centrifugal separation and filtration step for washing was cyclically repeated for 5 times.

To the filter unit, charged was 5.0 mM Tris-acetate buffer (pH=7.4, 0.30 mL) dissolving non-phosphorylated peptide p60c (p60c-src peptide 521–533, 14 nmol/mL) and phosphorylated peptide P-p60c (O-phosphoryl p60c-src peptide 521–533, 12 nmol/mL), as samples. The filter unit was brought to an equilibrium state for 5 minutes, and then, subjected to centrifugal separation at 2,000×g for 15 seconds and filtration. The obtained filtrate was taken out as a fraction 1.

Next, 5.0 mM Tris-acetate buffer (pH=7.4, 0.50M NaNO$_3$, 0.30 mL) was charged in the filter unit, and the filter unit was subjected to centrifugal separation at 2,000×g for 15 seconds and filtration for 3 times. The filtrate obtained after the first filtration was taken out as a fraction 2, the filtrate after the second filtration was taken out as a fraction 3, and the filtrate after the third filtration was taken out as a fraction 4.

Furthermore, 1.0 mM buffer containing phosphoric acid-sodium hydroxide (pH=7.4, 0.50M NaNO$_3$, 0.30 mL) was charged in the filter unit, and the filter unit was subjected to centrifugal separation at 2,000×g for 15 seconds and filtration for 2 times. The filtrate obtained after the first filtration was taken out as a fraction 5, and the filtrate after the second filtration was taken out as a fraction 6.

The contents of the peptide in the respective fractions 1 through 6 were quantitatively determined by high performance liquid chromatography (HPLC). The isolation/recovery rates of the respective peptides to the total amount are shown in Table 1.

TABLE 1

| Fraction No. | 1 | 2 | 3 | 4 | 5 | 6 |
|---|---|---|---|---|---|---|
| p60c (%) | 67 | 24 | 9 | 0 | 0 | 0 |
| P-p60c (%) | 0 | 0 | 0 | 0 | 83 | 17 |

Analyzing conditions according to HPLC:
column: Capcell Pak C18 type UG80, 4.6 mm (diameter)×150 mm
mobile phase: acetonitrile:water=14:86(v/v), 0.1%(v/v) of trifluoroacetic acid
flow rate: 1 mL/min.
column temperature: 40° C.
detecting method: UV 266 nm
retention time: P-p60c (5.3 min.). p60c (13.4 min.)

The above results reveal that the inventive complex compound can adsorb selectively a phosphorylated peptide and use of the inventive complex compound is advantageous in selectively isolating the phosphorylated peptide in a mixed sample of the phosphorylated peptide and the non-phosphorylated peptide.

Comparative Example 1

The suspension (0.3 mL) containing Streptavidin agarose (quantity of the bonded moiety of biotin; 60 to 120 nmol/mL) and a buffer (Sigma-Aldrich Co.) was charged in a centrifugal filter unit (volume: 0.5 mL, filter pore diameter: 0.22 μm). The filter unit was subjected to centrifugal separation at 2,000×g for 15 seconds, followed by filtration of the suspension. Then, 5.0 mM Tris-acetate buffer (pH=7.4, 0.30 mL) was charged in the filter unit, and the filter unit was subjected to centrifugal separation at 2,000×g for 15 seconds and filtration for washing. This centrifugal separation and filtration step for washing was cyclically repeated for 5 times.

A process similar to the process in Experiment Example 2 was conducted with use of samples equivalent to the samples used in Experimental Example 2, using a filter unit (in this Comparative Example, the inventive complex compound was not included). Thus, fractions 7 through 12 were obtained.

HPLC analysis was conducted with respect to the fractions 7 through 12 in a similar manner as Experimental Example 2. Results of the analysis are shown in Table 2.

TABLE 2

| Fraction No. | 7 | 8 | 9 | 10 | 11 | 12 |
|---|---|---|---|---|---|---|
| p60c (%) | 75 | 20 | 5 | 0 | 0 | 0 |
| P-p60c (%) | 83 | 17 | 0 | 0 | 0 | 0 |

The results in Table 2 reveal that separation of the phosphorylated peptide from the non-phosphorylated peptide is unsuccessful, even if a process similar to the process in Experimental Example 2 is conducted, because the inventive complex compound is not used.

Production Example 4-1

2-Acetoxymethyl-4-nitropyridine

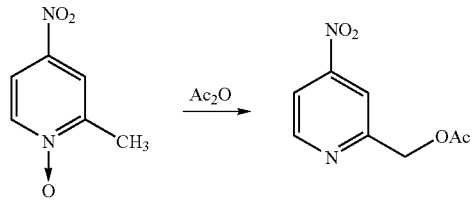

200 mL of acetic anhydride was heated to 100° C., followed by gradual addition of 2-methyl-4-nitropyridine N-oxide (25.0 g, 162 mmol). After the addition, the mixture was gradually heated, and was kept at 130° C. for 20 minutes. Then, the reaction mixture was cooled to 80° C., followed by dropwise addition of 200 mL of ethanol to stop the reaction.

After the reaction mixture was concentrated, the residue was put in water of 500 mL, and the pH of the mixture was adjusted to 9 by adding sodium hydrogencarbonate. After extraction with ethyl acetate twice (500 mL in the first extraction, and 200 mL in the second extraction), the obtained organic layers ware washed with 200 mL of water and 200 mL of brine. After concentration of the organic layer, the obtained crude product was purified by silica gel column chromatography, thereby to yield 7.68 g of the target compound.

$^1$H-NMR (CDCl$_3$, 300 MHz): δ 2.23(3H, s, COCH$_3$), 3.36(2H, s, CH$_2$Py), 7.97(1H, dd, Py), 8.07(1H, d, Py), 8.90(1H, d, Py)

Production Example 4-2

2-Hydroxymethyl-4-nitropyridine

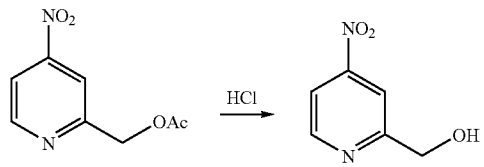

To 2-acetoxymethyl-4-nitropyridine (7.68 g, 39.2 mmol) obtained in Production Example 4-1, added was 30 mL of 10% hydrochloric acid. The mixture was reacted at 50° C. for 30 minutes. After the reaction mixture was cooled, the solution was poured into 200 mL of water, and the pH of the mixture was adjusted to 9 by adding sodium hydrogencarbonate. The mixture was extracted with 100 mL of ethyl acetate for three times, and the obtained organic layers were concentrated. The residue obtained by the concentration was purified by silica gel column chromatography, thereby to yield 4.70 g of the target compound.

$^1$H-NMR (CDCl$_3$, 300 MHz): δ 3.36(1H, t, OH), 4.94(2H, d, CH$_2$Py), 7.95(1H, ddt, Py), 8.09(1H, dt, Py), 8.86(1H, d, Py)

Production Example 4-3

2-Bromomethyl-4-nitropyridine

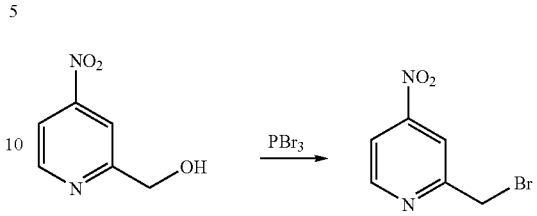

To a suspension of 2-hydroxymethyl-4-nitropyridine (1.00 g, 6.49 mmol) obtained in Production Example 4-2 in dried ether (40 mL), was added phosphorus tribromide (0.88 g, 3.24 mmol) at 0° C. dropwise. After the dropwise addition, the mixture was reacted at 0° C. for 2 hours, followed by reaction at 20° C. for 64 hours.

The reaction mixture was poured into 250 mL of ice-cold water, and the pH of the aqueous layer was adjusted to 8 by adding sodium hydrogencarbonate. After the ether layer and the aqueous layer were separated, the aqueous layer was extracted with 100 mL of ethyl acetate twice. The organic layers were collected, and dried over anhydrous sodium sulfate. After the solvent was distilled off, the crude product was purified by silica gal column chromatography, thereby to yield 0.80 g of the target compound.

$^1$H-NMR (CDCl$_3$, 300 MHz): δ 4.66(2H, s, CH$_2$Py), 7.96(1H, dd, Py), 8.19(1H, dd, Py), 8.88(1H, dd, Py)

Production Example 4-4

N,N,N'-Tri(2-pyridylmethyl)-N'-(4-nitro-2-pyridylmethyl)-1,3-diaminopropane-2-ol

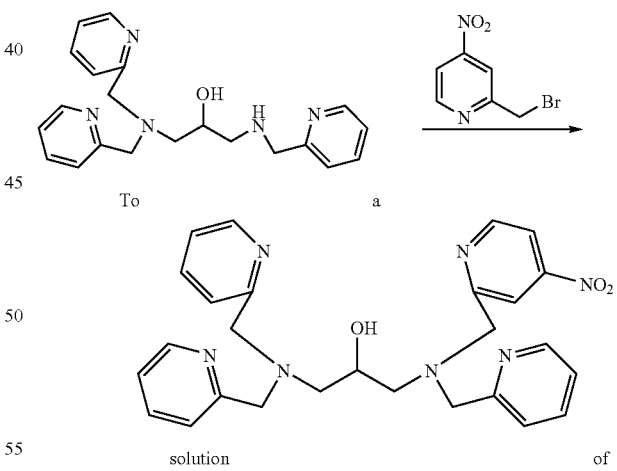

To a solution of N,N,N'-tri(2-pyridylmethyl)-1,3-diaminopropane-2-ol (2.65 g, 7.28 mmol) obtained in Production Example 1-2 in dried dimethylformamide (40 mL), was added anhydrous potassium carbonate (2.02 g, 14.6 mmol), and the mixture was heated to 55° C. Then, a solution of the 2-bromomethyl-4-nitropyridine (1.58 g, 7.28 mmol) obtained in Production Example 4-3 in dried dimethylformamide (20 mL) was added dropwise at the same temperature, i.e., 55° C. After the mixture was reacted at 55° C. for 1.5 hours, the mixture was cooled.

The reaction mixture was poured into 200 mL of water, and the pH of the mixture was adjusted to 8 by adding 1N hydrochloric acid. After extraction with 400 mL of ethyl acetate for three times, the organic layer was washed with 250 mL of brine. After being dried over anhydrous magnesium sulfate, the organic layer was concentrated. After the solvent was distilled off, the crude product was purified by silica gel column chromatography, thereby to yield 3.30 g of the target compound.

$^1$H-NMR (CDCl$_3$, 300 MHz): δ 2.60–2.78(4H, m, NCH$_2$), 3.84–3.96(6H, m, CH$_2$Py), 3.96–4.03(1H, m, OCH), 4.07 (2H, s, CH$_2$Py), 7.09–7.14(3H, m, Py), 7.34(3H, t, Py), 7.55–7.62(3H, m, Py), 7.80(1H, dd, Py), 8.22(1H, d, Py), 8.49–8.52(3H, m, Py), 8.76(1H, dd, Py)

Production Example 4-5

N,N,N'-Tri(2-pyridylmethyl)-N'-(4-azide-2-pyridylmethyl)-1,3-diaminopropane-2-ol

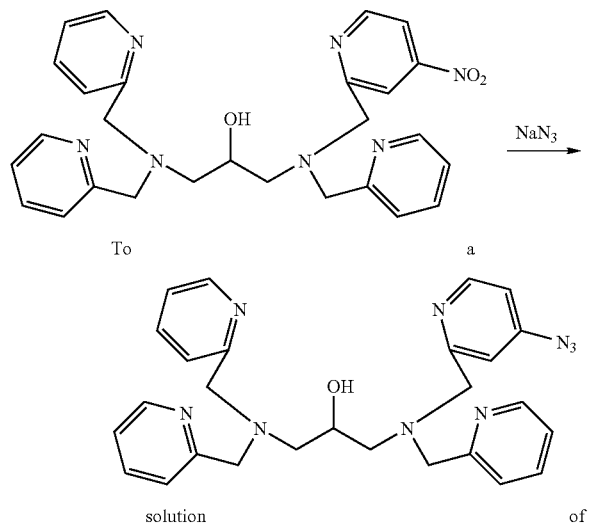

To a solution of

N,N,N'-tri(2-pyridylmethyl)-N'-(4-nitro-2-pyridylmethyl)-1,3-diaminopropane-2-ol (1.01 g, 2.00 mmol) obtained in Production Example 4-4 in dried tetrahydrofuran (17 mL), was added sodium azide (156 mg, 2.40 mmol) in water (3.3 mL) dropwise at room temperature. The reaction mixture was heated to 50° C., and reacted at the same temperature, i.e., 50° C. for 17 hours.

After the mixture was cooled, the aqueous layer was extracted with 10 mL of chloroform twice. The extracts were collected and concentrated, and the resulting crude product obtained was purified by silica gel column chromatography, thereby to yield 980 mg of the target compound.

$^1$H-NMR (CDCl$_3$, 300 MHz): δ 2.58 2.74(4H, m, NCH$_2$), 3.83–3.92(8H, m, CH$_2$Py), 3.92–4.01(1H, m, OCH), 6.74 (1H, dd, Py), 7.09–7.14(3H, m, Py), 7.20(1H, d, Py), 7.32–7.36(3H, m, Py), 7.55–7.60(3H, m, Py), 8.39(1H, d, Py), 8.49–8.52(3H, m, Py)

Production Example 4-6

N,N,N'-Tri(2-pyridylmethyl)-N'-(4-amino-2-pyridylmethyl)-1,3-diaminopropane-2-ol

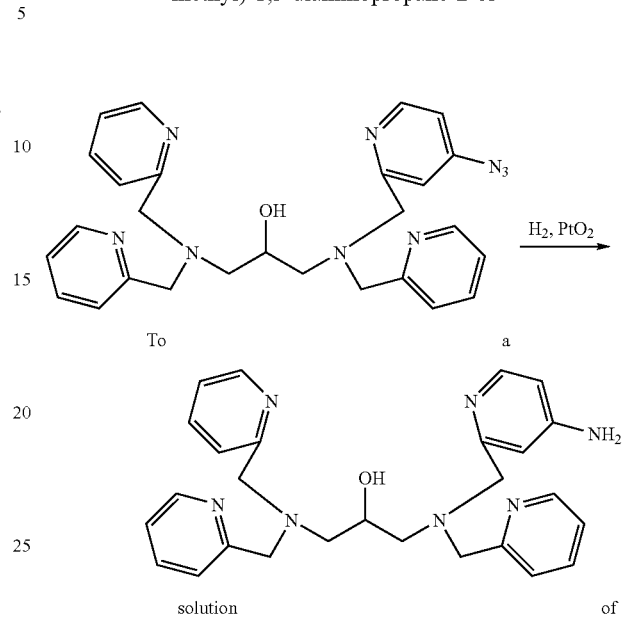

To a solution of

N,N,N'-tri(2-pyridylmethyl)-N'-(4-azide-2-pyridylmethyl)-1,3-diaminopropane-2-ol (980 mg, 1.98 mmol) obtained in Production Example 4-5 in ethanol (20 mL), was added 100 mg of platinum oxide. The mixture was reacted under hydrogen pressure of 30 kPa for 2 hours. After the catalyst (platinum oxide) was removed by filtration, the filtrate was concentrated, and the resulting crude product was purified by silica gel column chromatography, thereby to yield 690 mg of the target compound.

$^1$H-NMR (CDCl$_3$, 300 MHz): δ 2.43–2.71(4H, m, NCH$_2$), 3.66–3.92(8H, m, CH$_2$Py), 3.92–4.01(1H, m, OCH), 6.35 (1H, dd, Py), 6.63(1H, d, Py), 7.08–7.14(3H, m, Py), 7.27–7.39(3H, m, Py), 7.54–7.62(3H, m, Py), 8.10(1H, d, Py), 8.49–8.50(3H, m, Py)

Production Example 4-7

N,N,N'-Tri(2-pyridylmethyl)-N'-(4-D-biotinamido-2-pyridylmethyl)-1.3-diaminopropane-2-ol

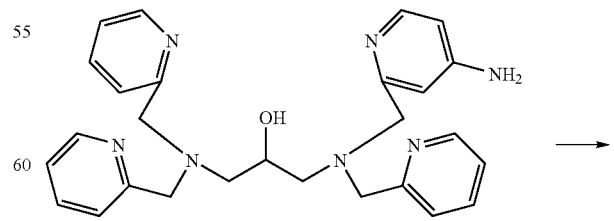

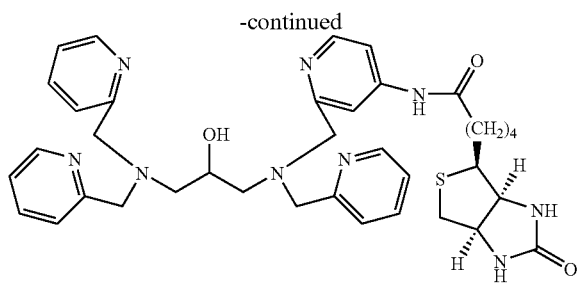

62.4 mg of D-biotin (0.26 mmol) was suspended into 5 mL of dichloromethane, followed by addition of 5.2 mg of 4-dimethylaminopyridine (0.04 mmol) and 35.8 μL of triethylamine (0.26 mmol) at room temperature. To this mixture, was added a solution of N,N,N'-tri(2-pyridylmethyl)-N'-(4-amino-2-pyridylmethyl)-1,3-diaminopropane-2-ol (100 mg, 0.21 mmol) obtained in Production Example 4-6 in dichloromethane (2 mL) dropwise at room temperature. After the dropwise addition, 1-ethyl-3-(3-dimethylaminopropyl)carbodiimide hydrochloride (49.0 mg, 0.26 mmol) was added at room temperature. The reaction mixture was heated, and reacted under reflux for 5 hours. To the reaction mixture, were added D-biotin (6.0 mg, 0.02 mmol), 1-ethyl-3-(3-dimethylaminopropyl)carbodiimide hydrochloride (10.0 mg, 0.05 mmol), and 2 mL of dichloromethane, followed by reaction under reflux for 6 hours.

After the reaction mixture cooled, the mixture was poured into 40 mL of water. After extraction with 30 mL of chloroform for three times, the organic layers were washed with 30 mL of water twice and 30 mL of brine. After the organic layer was dried over anhydrous magnesium sulfate and concentrated, the resulting crude product was purified by HPLC, thereby to yield 62.5 mg of the target compound.

$^1$H-NMR (CDCl$_3$, 300 MHz): δ 1.37–1.45(2H, m, CH$_2$), 1.53–1.71(4H, m, CH$_2$), 2.19–2.25(2H, m, COCH$_2$), 2.62–2.75(5H, m, NCH$_2$, SCH$_2$), 2.87–2.93(1H, dd, SCH$_2$), 3.09–3.15(1H, m, SCH), 3.67–3.80(9H, m, OCH, NCH$_2$Py), 4.28–4.32(1H, m, NCH), 4.48–4.52(1H, m, NCH), 5.15–5.40(2H, m, NHCO) 5.89(1H, bs, NHCO) 6.48–6.50 (1H, m, Py), 6.72–6.76(1H, m, Py), 7.13–7.17(3H, m, Py), 7.27–7.29(1H, m, Py), 7.37(2H, d, Py), 7.56–7.66(3H, m, Py), 8.00(1H, dd, Py), 8.49–8.50 (3H, m, Py)

Figure 5:
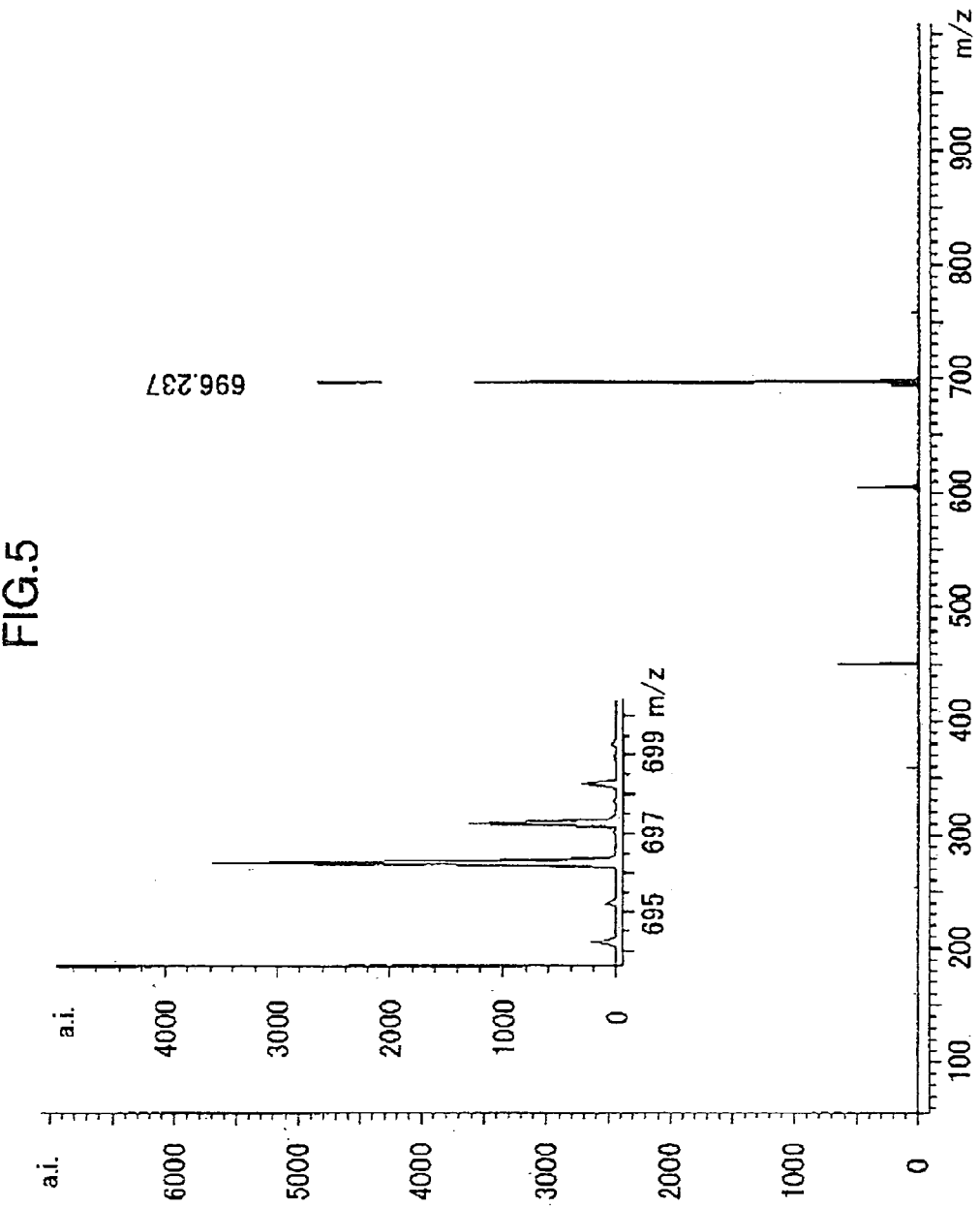
FIG. 5 is an illustration showing a result of examination by the MALDI-TOF mass spectrometer regarding the raw material compound used in producing the inventive compound having biotin as a labeling group, as well as an enlarged illustration showing a certain region of the examination result.

This compound was examined by the MALDI-TOF mass spectrometer using α-cyano-4-hydroxycinnamic acid (CHCA) as a matrix. A result of measurement is shown in FIG. 5. As is obvious from FIG. 5, a molecular ion peak 696.2 of proton adduct ion (M$^+$+1) was observed.

Production Example 5-1

Methyl 6-aminohexanoate hydrochloride

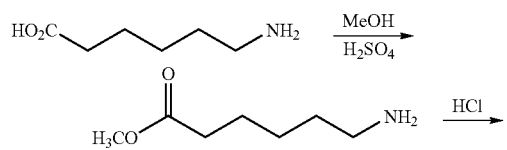

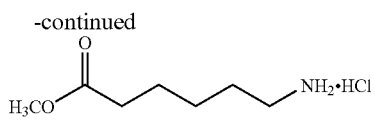

To a suspension of 6-aminohexanoic acid (10.0 g, 76.2 mmol) in methanol (300 mL), was added 5.51 g of concentrated sulfuric acid. The mixture was heated and reacted for 8 hours, while the water formed along with the progress of esterification distilled off with methanol and 60 mL of methanol was added four times on cue. The reaction mixture was cooled, and the pH of the mixture was adjusted to 6.2 by adding 28% methanol solution of sodium methoxide. The solvent was distilled off, the residue was added to 500 mL of water, and the pH of the mixture was adjusted to 10.3 by adding sodium carbonate. After extraction with 350 mL of dichloromethane for three times, the extract was dried over anhydrous magnesium sulfate. Thereafter, the solvent was distilled off, thereby to yield methyl 6-aminohexanoate.

The methyl 6-aminohexanoate was dissolved in 40 mL of dioxane, followed by addition of 7.1 mL of 4N-hydrochloride solution of dioxane. After the mixture was stirred at room temperature for 30 minutes, the solvent was distilled off, followed by addition of ether to the residue. The precipitated crystals were isolated by filtration and dried under reduced pressure to yield 3.3 g of the target compound.

$^1$H-NMR (DMSO-d$_6$, 300 MHz): δ 1.26–1.36(2H, m, CH$_2$), 1.48–1.61(4H, m, CH$_2$), 2.31(2H, t, CH$_2$CO), 2.73 (2H, t, CH$_2$N), 3.59(3H, s, CH$_3$), 8.1(3H, bs, NH$_3$)

Production Example 5-2

5-Carbomethoxypentyl-D-biotinamide

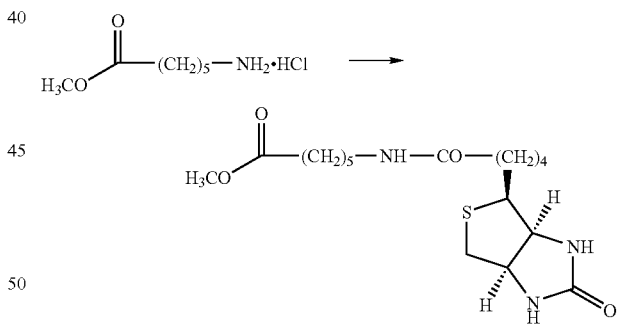

To a solution of methyl 6-aminohexanoate hydrochloride (1.00 g, 5.50 mmol) obtained in Production Example 5-1 in dimethylformamide (40 mL), were added triethylamine (1.20 g, 11.8 mmol) and 4-dimethylaminopyridine (137 mg, 1.1 mmol). Furthermore, were added D-biotin (1.34 g, 5.50 mmol) and 1-ethyl-3-(3-dimethylaminopropyl)carbodiimide hydrochloride (1.42 g, 7.42 mmol) The mixture was reacted at temperature from 35 to 45° C. for 23 hours.

The reaction mixture was poured into 300 mL of water, and extracted with 150 mL of chloroform for 5 times. After the extracts were dried over anhydrous magnesium sulfate and the solvent was distilled off. The resulting crude product was purified by silica gel column chromatography, thereby to yield 1.04 g of the target compound.

$^1$H-NMR (DMSO-d$_6$, 300 MHz); δ 1.18–1.65(12H, m, CH$_2$), 2.04(2H, t, CH$_2$CO), 2.28(2H, t, CH$_2$CO), 2.57(1H, d, CH$_2$S), 2.82(1H, dd, CH$_2$S), 3.00(1H, dt, NHCO), 3.06–3.12(1H, m, CH$_2$S), 3.58(3H, S, OCH$_3$), 4.09–4.15 (1H, m, CHN), 4.28–4.32(1H, m, CHN), 6.35(1H, bs, NHCO), 6.41(1H, bs, NHCO), 7.72(1H, t, NHCO)

Production Example 5-3

5-Carboxypentyl-D-biotinamide

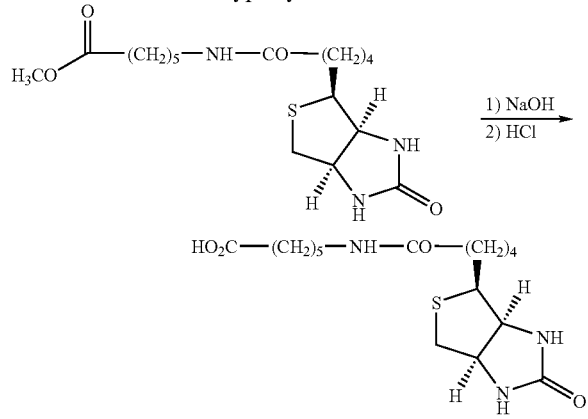

To a mixture of 25 mL of tetrahydrofuran and 25 mL of methanol, was dissolved 5-carbomethoxypentyl-D-biotinamide (800 mg, 2.15 mmol) obtained in Production Example 5-2, followed by addition of a solution of sodium hydroxide (2.33 g, 58.3 mmol) in water (12.5 mL) dropwise at room temperature. After the addition was completed, the mixture was heated to 40° C. and reacted for 2 hours.

After cooling, the reaction mixture was concentrated, followed by addition of 60 mL of water. Then, 1N hydrochloric acid was added, and the pH of the mixture was adjusted to 2.0. The precipitated crystals were isolated by filtration and washed with water. The obtained crystals were dried in vacuo, thereby to yield 724 mg of the target compound.

$^1$H-NMR (DMSO-d$_6$, 300 MHz): δ 1.17–1.67(12H, m, CH$_2$), 2.04(2H, t, CH$_2$CO), 2.19(2H, t, CH$_2$CO), 2.57(1H, d, CH$_2$S), 2.82(1H, dd, CH$_2$S), 3.00(1H, dt, NHCO), 3.06–3.12(1H, m, CH$_2$S), 4.13(1H, t, CHN), 4.30(1H, t, CHN), 6.36(1H, bs, NHCO), 6.43(1H, bs, NHCO), 7.74(1H, t, NHCO), 11.95(1H, bs, CO$_2$H)

Production Example 5-4

N,N,N'-Tri(2-pyridylmethyl)-N'-[4-(6-D-biotinamidohexacarboxyamido)-2-pyridylmethyl]-1,3-diaminopropane-2-ol

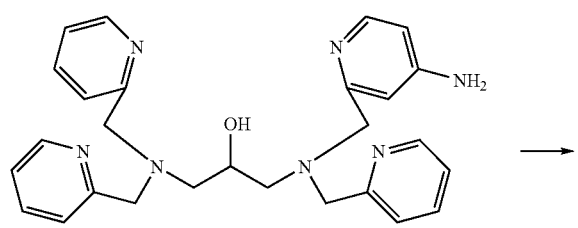

-continued

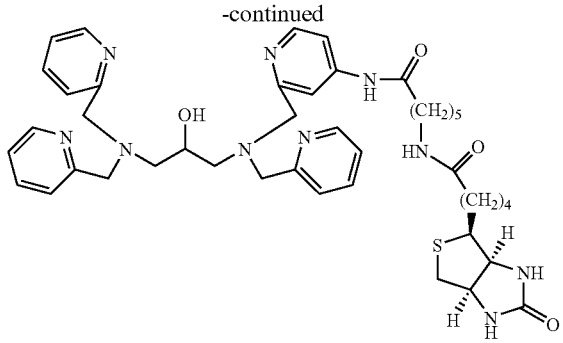

To a solution of 5-carboxypentyl-D-biotinamide (99.0 mg, 0.27 mmol) obtained in Production Example 5-3 in dried dimethylformamide, were added triethylamine (38.1 μL, 0.27 mmol) and 4-dimethylaminopyridine (5.7 mg, 0.04 mmol), followed by addition of a solution of N,N,N'-tri(2-pyridylmethyl)-N'-(4-amino-2-pyridylmethyl)-1,3-diaminopropane-2-ol (100 mg, 0.21 mmol) obtained in Production Example 4-6 in dried dimethylformamide (1 mL) dropwise. Further, was added 1-ethyl-3-(3-dimethylaminopropyl)carbodiimide hydrochloride (51.7 mg, 0.27 mmol). The mixture was reacted at 40° C. for 24 hours. To the reaction mixture, added were 8.9 μL of triethylamine (0.06 mmol), 22.8 mg of 5-carboxypentyl-D-biotinamide (0.06 mmol) and 12.2 mg of 1-ethyl-3-(3-dimethylaminopropyl) carbodiimide hydrochloride (0.06 mmol). The mixture was reacted at 40° C. for 6 hours.

After the reaction mixture was cooled, the mixture was poured into 150 mL of water, followed by addition of sodium chloride to attain saturation. After extraction with 40 mL of chloroform for 5 times, the organic layers were washed with 150 mL of water twice and 150 mL of brine. After extract was dried over anhydrous magnesium sulfate, the solvent was distilled off. The crude product obtained was purified by HPLC, thereby to yield 37.5 mg of the target compound.

$^1$H-NMR (CDCl$_3$, 300 MHz): δ 1.30–1.80(12H, m, CH$_2$), 2.14–2.25(4H, m, COCH$_2$), 2.60–2.76(5H, m, NCH$_2$, CH$_2$S), 2.87(1H, dd, CH$_2$S), 3.10–3.25(3H, m, CH$_2$NHCO, SCH), 3.68–3.82(9H, m, NCH$_2$Py, OCH), 4.28–4.33(1H, m, NCH), 4.45–4.52(1H, m, NCH), 5.27(1H, bs, NHCO), 5.50 (1H, bs, NHCO), 5.60(1H, bs, NHCO) 6.22(1H, bs, NHCO), 6.52–6.57(1H, m, Py), 6.72–6.75(1H, m, Py), 7.16(3H, t, Py), 7.27–7.30(1H, m, Py), 7.37(2H, d, Py), 7.57–7.66(3H, m, Py), 7.99(1H, d, Py), 8.46–8.52(3H, m, Py)

Figure 6:
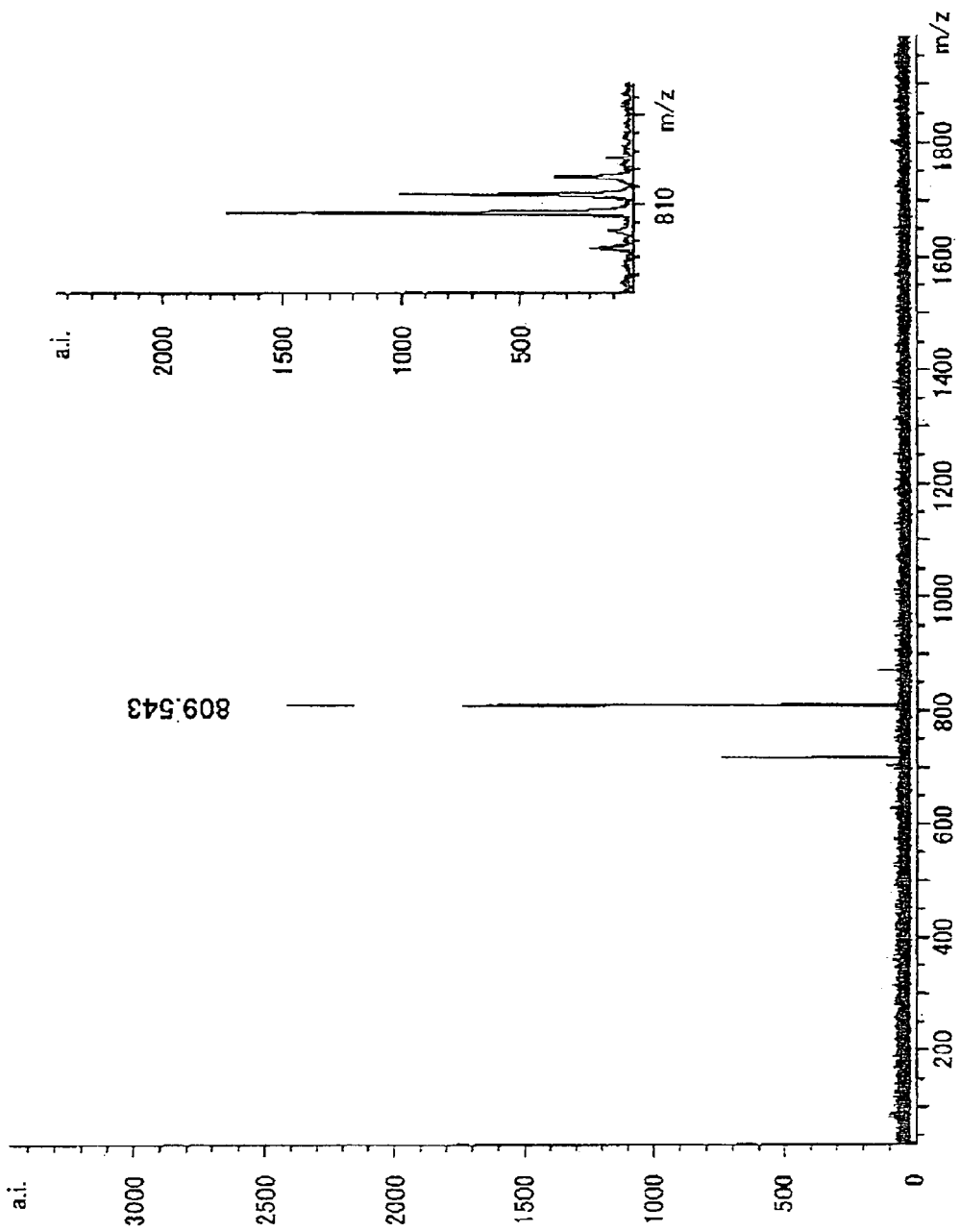
FIG. 6 is an illustration showing a result of examination by the MALDI-TOF mass spectrometer regarding the raw material compound used in producing the inventive compound having biotin as a labeling group, as well as an enlarged illustration showing a certain region of the examination result.

This compound was measured by the MALDI-TOF mass spectrometer using CHCA as a matrix. A result of measurement is shown in FIG. 6. As is obvious from FIG. 6, a molecular ion peak 809.5 of proton adduct ion (M$^+$+1) was observed Production Example 6-1

2-Bromomethyl-3-hydroxypyridine

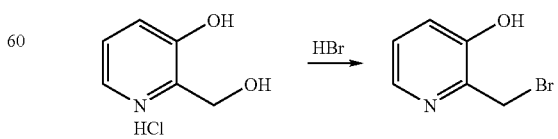

To 25% acetic acid solution of hydrogen bromide (12.8 g, 39.6 mmol), was added 3-hydroxy-2-hydroxymethylpyridine hydrochloride (5.0 g, 54.7 mmol). The mixture was reacted at 110° C. for 1 hour. Furthermore, was added 25% acetic acid solution of hydrogen bromide (4.90 g, 15.1 mmol) dropwise, and the mixture was reacted for 2 hours.

After cooling, the reaction mixture was poured into 50 mL of water, and the pH of the mixture was adjusted to 8 by adding saturated aqueous sodium hydrogencarbonate solution. After extraction with 50 mL of dichloromethane for four times, the dichloromethane layers were concentrated. The crude product after the concentration was purified by silica gel column chromatography, thereby to yield 1.36 g of the target compound.

$^1$H-NMR (CDCl$_3$, 300 MHz): δ 5.31(2H, s, CH$_2$Br), 7.20–7.32(2H, m, Py), 8.18–8.21(1H, m, Py), 8.55(1H, bs, OH)

Production Example 6-2

N,N,N'-Tri(2-pyridylmethyl)-N'-(3-hydroxy-2-pyridylmethyl)-1,3-diaminopropane-2-ol In dimethylformamide (15 mL), were dissolved N,N,N'-tri(2-pyridylmethyl)-1,3-diaminopropane-2-ol (1.00 g, 2.75 mmol) obtained in Production Example 1-2 and 2-bromomethyl-3-hydroxypyridine (633 mg, 3.37 mmol) obtained in Production Example 6-1, followed by addition of potassium carbonate (760 mg, 5.50 mmol). The mixture was reacted at 50° C. for 2 hours and cooled.

The reaction mixture was poured into 100 mL of water, and the pH of the mixture was adjusted to 8 by adding 1N hydrochloric acid. After extraction with 100 mL of ethyl acetate for three times, the organic layers were washed with 100 mL of water and 100 mL of brine, and dried over anhydrous sodium sulfate. The obtained crude product was purified and collected by HPLC, thereby to yield 660 mg of the target compound.

$^1$H-NMR (CDCl$_3$, 300 MHz): δ 2.51–2.69(4H, m, NCH$_2$), 3.71–4.08(9H, m, CH$_2$Py, OCH), 7.05–7.14(4H, m, Py), 7.15–7.19(1H, t, Py), 7.23–7.28(3H, m, Py), 7.55(2H, dt, Py), 7.64(1H, dt, Py), 7.91(1H, dd, Py), 8.48–8.55(3H, m, Py)

Production Example 6-3

N,N,N'-Tri(2-pyridylmethyl)-N'-(3-D-biotinyloxy-2-pyridylmethyl)-1.3-diaminopropane-2-ol

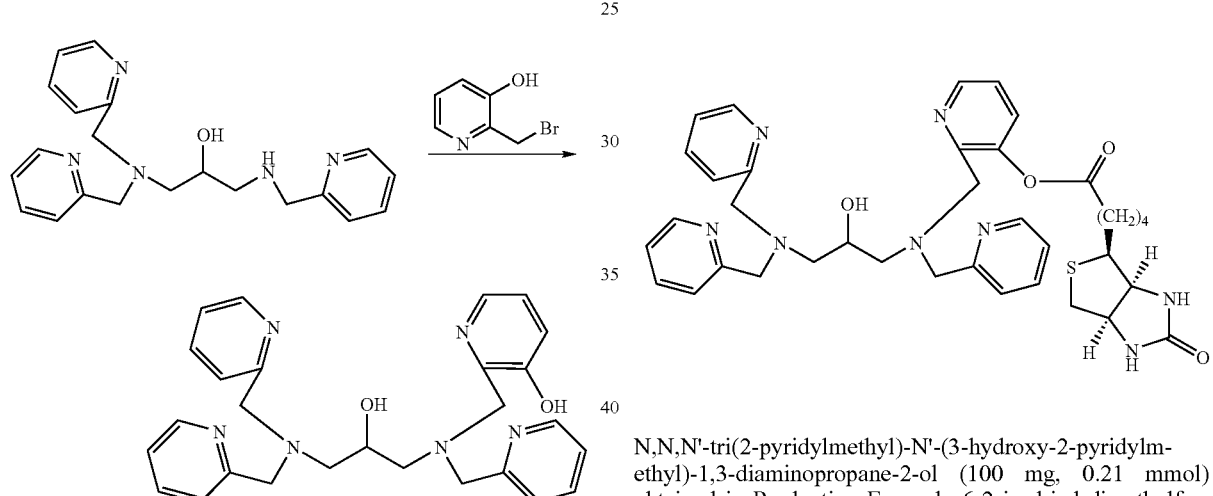

N,N,N'-tri(2-pyridylmethyl)-N'-(3-hydroxy-2-pyridylmethyl)-1,3-diaminopropane-2-ol (100 mg, 0.21 mmol) obtained in Production Example 6-2 in dried dimethylformamide (5 mL), was added sodium hydride (dispersion in mineral oil) (9.0 mg, 0.23 mmol) at 3° C. After the temperature was returned to room temperature, the mixture was reacted at room temperature for 30 minutes, followed by addition of a solution of N-succinimidyl D-biotinate (79.8 mg, 0.23 mmol) in dried dimethylsulfoxide (1 mL) dropwise.

After the dropwise addition, the mixture was reacted at room temperature for 3.5 hours and poured into 100 mL of water. After extraction with 300 mL of chloroform for three times, the chloroform layers were dried over anhydrous sodium sulfate. After the solvent was distilled off, the crude product was collected and purified by HPLC, thereby to yield 63.6 mg of the target compound.

$^1$H-NMR (CDCl$_3$, 300 MHz): δ 1.43–1.56(2H, m, CH$_2$), 1.60–1.85(4H, m, CH$_2$), 2.53(2H, t, COCH$_2$), 2.58–2.68 (4H, m, NCH$_2$), 2.71–2.77(1H, m, SCH$_2$), 2.91(1H, dd, SCH$_2$), 3.13–3.19(1H, m, SCH), 3.76–3.99(9H, m, OCH, NCH$_2$Py), 4.28–4.36(1H, m, NCH), 4.47–4.53(1H, m, NCH), 5.16(1H, bs, NHCO) 5.93(1H, d, NHCO) 7.08–7.14 (3H, m, Py), 7.20(1H, dd, Py), 7.33–7.42(4H, m, Py), 7.52–7.62(3H, m, Py), 8.42(1H, dd, Py), 8.51(3H, m, Py)

Production Example 6-4

Solution Containing the Inventive Zinc Complex

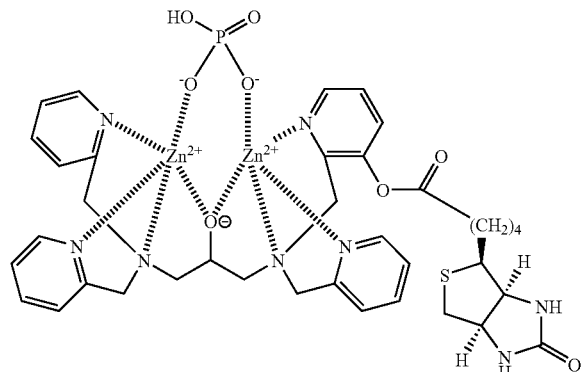

C37H44N8O8PSZn2
Mol. Wt: 922.61
Exact Mass: 919.13

Figure 7:
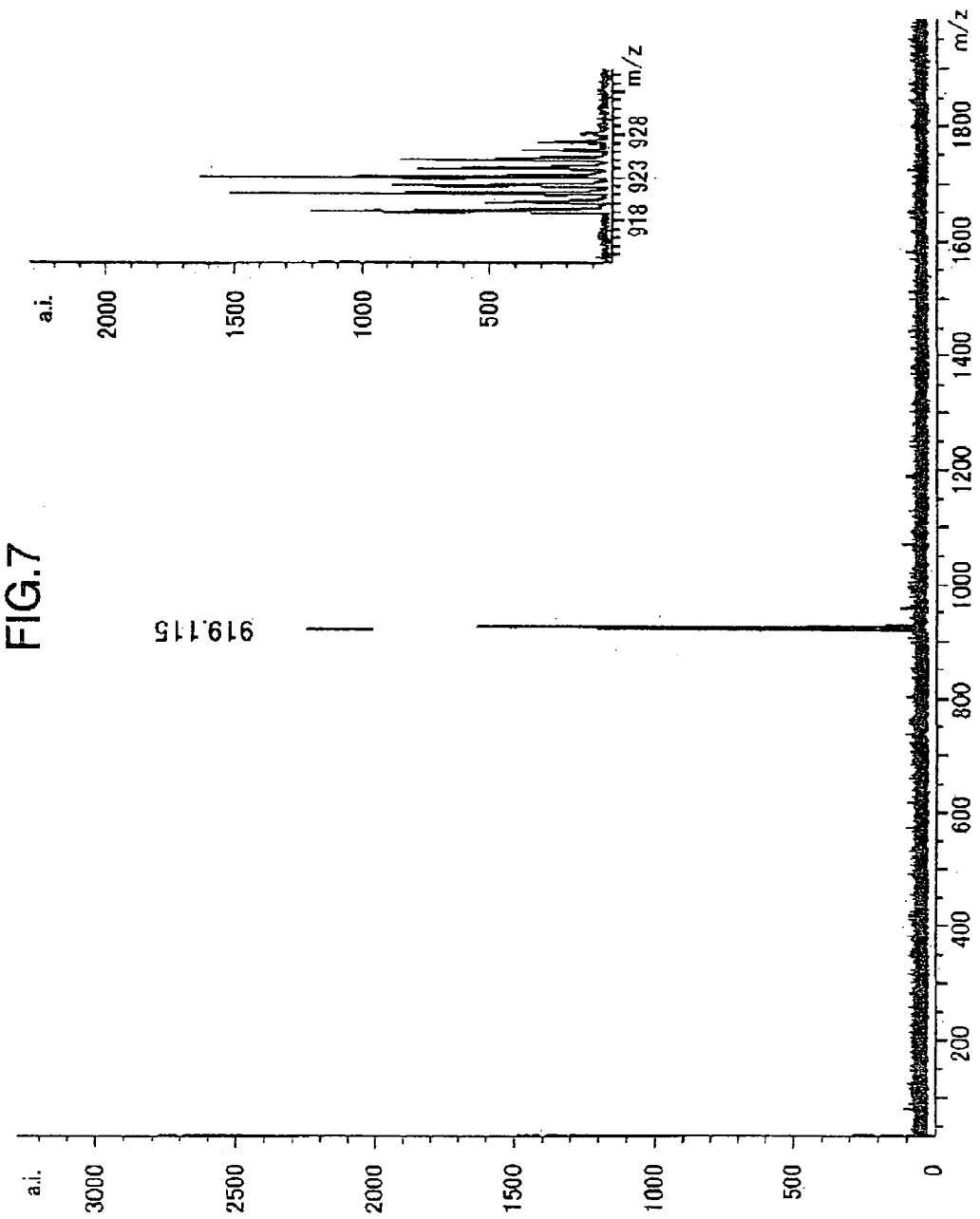
FIG. 7 is an illustration showing a result of examination by the MALDI-TOF mass spectrometer regarding a zinc complex according to the present invention, as well as an enlarged illustration showing a certain region of the examination result.

To an acetonitrile solution (66.7 μL) containing 200 nmol of N,N,N'-tri(2-pyridylmethyl)-N'-(3-D-biotinyloxy-2-pyridylmethyl)-1,3-diaminopropane-2-ol obtained in Production Example 6-3, added was 40.1 μL of 100 mM zinc nitrate aqueous solution, followed by addition of 560 μL of phosphoric acid buffer (pH=6.86). The solution was analyzed by the MALDI-TOF mass spectrometer by using 2',4'-6'-trihydroxyacetophenone (THAP) as a matrix, and the zinc complex was identified. A result of measurement by the MALD-TOF mass spectrometer is shown in FIG. 7. As shown in FIG. 7, a molecular ion peak at 919.1 (exact mass: 919.13) was observed.

Production Example 7-1

N,N,N'-Tri(2-pyridylmethyl)-N'-[5-N'''-(2-dansylaminoethyl)carbamoyl-2-pyridylmethyl]-1,3-diaminopropane-2-ol

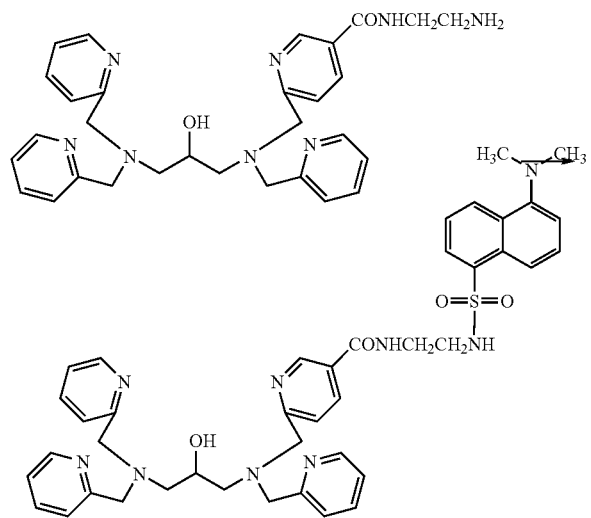

In dried acetonitrile (9 mL), was dissolved N,N,N'-tri(2-pyridylmethyl)-N'-[5-N'''-2-(aminoethyl)carbamoyl-2-pyridylmethyl]-1,3-diaminopropane-2-ol (1.1 g, 2.1 mmol) obtained in Production Example 1-4, followed by addition of dansyl chloride (840 mg, 3.1 mmol). The reaction mixture was heated and reacted at 50° C. for 3 hours. After the reaction mixture was concentrated, the crude product was purified by silica gel column chromatography, thereby to yield 1.30 g of the target compound.

$^1$H-NMR (CDCl$_3$, 500 MHz): δ 2.57(1H, dd, CH$_2$), 2.60(1H, dd, CH$_2$), 2.67(1H, dd, CH$_2$), 2.69(1H, dd, CH$_2$), 2.85(6H, s, NCH$_3$), 3.17(2H, dd, NCH$_2$CH$_2$N), 3.50(2H, dd, NCH$_2$CH$_2$N), 3.88(8H, dd, NCH$_2$Py), 3.83–3.92(1H, m, OCH), 6.31(1H, m, SO$_2$NH), 7.11(1H, d, Ar), 7.13(3H, ddd, Py), 7.35(3H, d, Py), 7.36(1H, d, Py), 7.42(1H, m, CONH), 7.46(1H, dd, Ar), 7.49(1H, dd, Ar), 7.60(2H, dt, Py), 7.60 (1H, dt, Py), 7.90(1H, dd, Py), 8.23(1H, dd, Ar), 8.27(1H, d, Ar), 8.49(2H, ddd, Py), 8.50(1H, ddd, Py), 8.51(1H, dd, Ar), 8.80(1H, d, Py) $^{13}$C-NMR (CDCl$_3$, 125 MHz): 39.9 (NCH$_2$CH$_2$N), 42.7(NCH$_2$CH$_2$N), 45.3(NCH$_3$), 59.0(CH$_2$), 59.1(CH$_2$), 60.6(CH$_2$Py), 60.7(CH$_2$Py), 61.3(CH$_2$Py), 67.1 (CHO), 115.2(Ar), 118.6(Ar), 122.1(Py), 122.8(Py), 123.2 (Ar), 123.2(Py), 128.1(Ar), 128.5(Ar), 129.5(Ar), 129.6 (Ar), 129.9(Py), 130.6(Ar), 134.5(Ar), 135.4(Py), 136.5 (Py), 136.6(Py), 147.6(Py), 148.9(Py), 149.0(Py), 152.0 (Ar), 159.1(Py), 159.1(Py), 162.8(Py), 166.2(CONH)

Production Example 7-2

Solution Containing the Incentive Zinc Complex

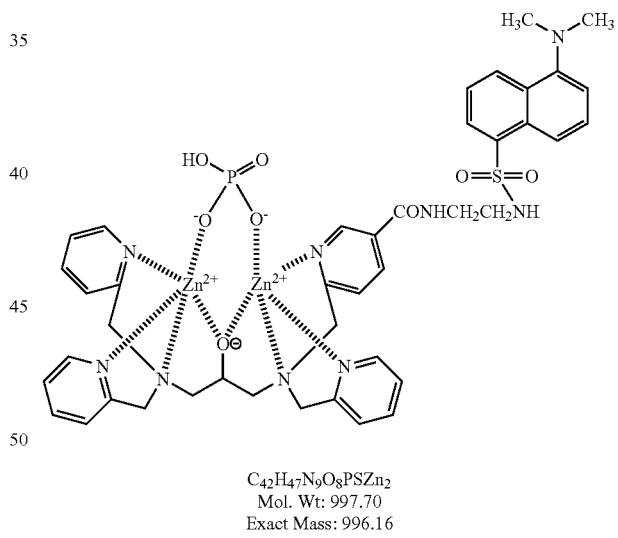

C42H47N9O8PSZn2
Mol. Wt: 997.70
Exact Mass: 996.16

Figure 8:
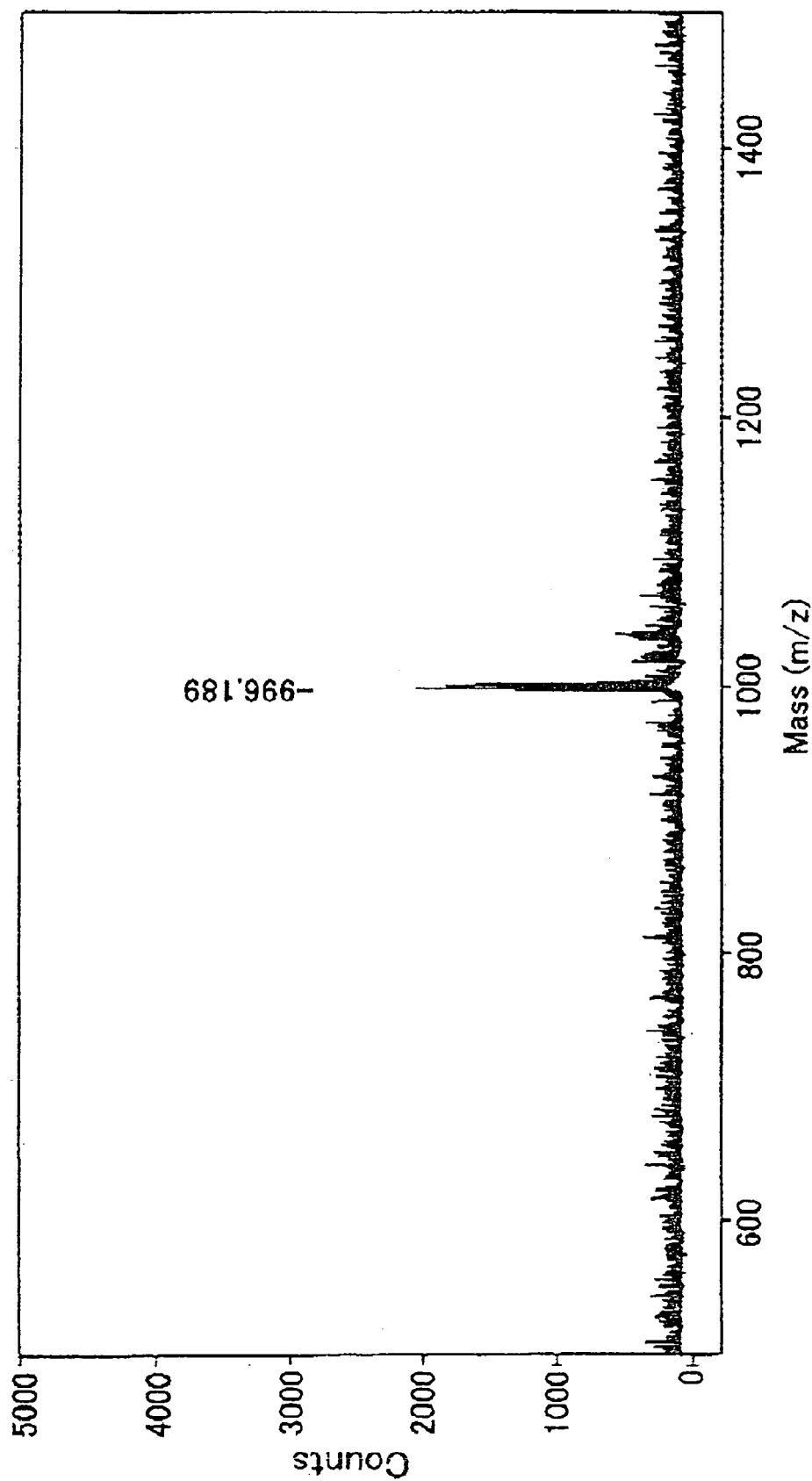
FIG. 8 is an illustration showing a result of examination by the MALDI-TOF mass spectrometer regarding a zinc complex according to the present invention.

In a phosphoric acid buffer (pH=6.86), dissolved was 200 nmol of N,N,N'-tri(2-pyridylmethyl)-N'-[5-N'''-(2-dansylaminoethyl)carbamoyl-2-pyridylmethyl]-1,3-diaminopropane-2-ol obtained in Production Example 7-1 to prepare 3 mM solution, followed by addition of zinc nitrate of 2 equivalents to the solution. The solution was analyzed by the MALDI-TOF mass spectrometer by using THAP as a matrix, and the zinc complex was identified. A result of measurement by the MALDI-TOF mass spectrometer is shown in FIG. 8. As shown in FIG. 8, a molecular ion peak at 996.2 (exact mass: 996.16) was observed.

Production Example 8-1

N,N,N'-Tri(2-pyridylmethyl)-N'-[5-N"-(2-N-5-fluo-resceinylthioureidoethyl)carbamoyl-2-pyridylmethyl]-1,3-diaminopropane-2-ol

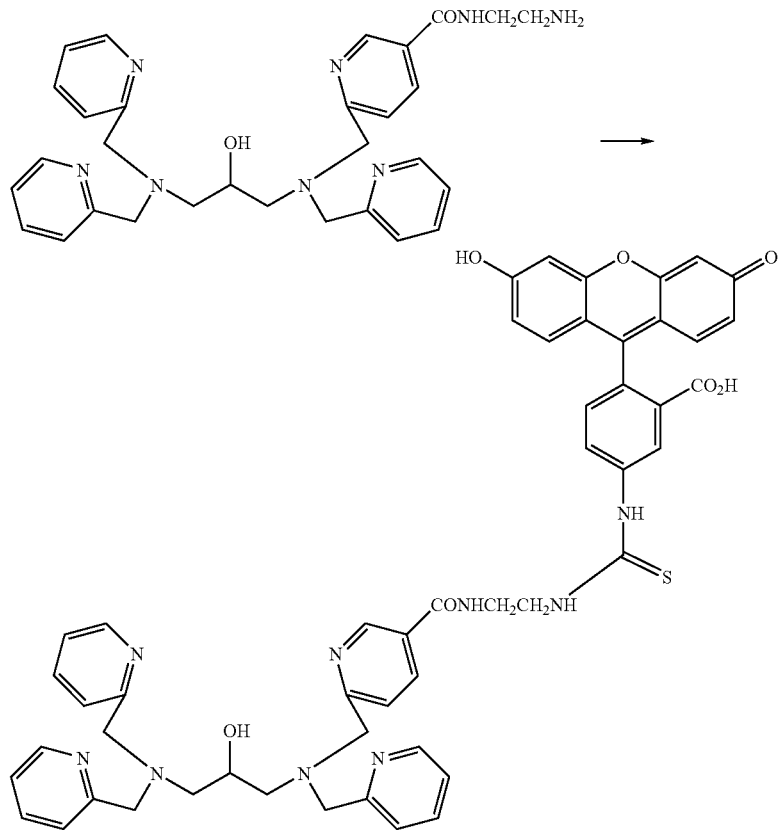

In dried dimethylformamide (150 mL), was dissolved N,N,N'-tri(2-pyridylmethyl)-N'-[5-N"-(2-aminoethyl)carbamoyl-2-pyridylmethyl]-1,3-diaminopropane-2-ol (950 mg, 1.76 mmol) obtained in Production Example 1-4, followed by addition of dried pyridine (38 mL). Then, a solution of fluorescein-5-isothiocyanate (750 mg, 1.92 mmol) in dried dimethylformamide (150 mL) was added dropwise, and the mixture was reacted at room temperature for 3 hours. After the reaction mixture was concentrated, the crude product was purified by silica gel column chromatography, thereby to yield 961 mg of the target compound.

$^1$H-NMR (DMSO-$d_6$, 300 MHz): δ 2.33–2.43(2H, m, CH$_2$), 2.50–2.61(2H, m, CH$_2$), 3.38–3.57(4H, m, NCH$_2$CH$_2$N), 3.67–3.92(9H, m, NCH$_2$Py, CHO), 6.52–6.67 (6H, m, Ar), 7.16–7.23(3H, m, Py), 7.17(1H, d, Ar), 7.34–7.41(3H, m, Py), 7.52(1H, d, Py), 7.69(3H, dt, Py), 7.68–7.77(1H, m, Ar), 8.14(1H, dd, Py), 8.24(1H, d, Ar), 8.41–8.46(3H, m, Py), 8.78(1H, m, NHCO), 8.92(1H, d, Py)

Experimental Example 3

10% Native-polyacrylamide Gel Electrophoresis

First, prepared were gels for electrophoresis, pH buffer for electrophoresis, and a coloring solution for dissolving samples under the same condition as in Experimental Example 1.

Next, 2 μg each of 1: Bovine Serum Albumin, 2: Human Serum Albumin, 3: carbonic anhydrase, 4: β-galactosidase, 5: α-casein (phosphorylated), 6: α-casein (de-phosphorylated), 7: β-casein (phosphorylated), 8: β-casein (de-phosphorylated), 9: pepsin (phosphorylated), and 10: pepsin (de-phosphorylated) was dissolved in the coloring solution to prepare samples. The respective samples were plotted on the gel. Then, a constant electric current of 40 mA was applied until the coloring marker was flowed.

The obtained gel was immersed in a 10 mM Tris-acetate buffer (pH=7.4) containing 1 μM of N,N,N'-tri(2-pyridylmethyl)-N'-[5-N"-(2-N-5-fluoresceinylthioureidoethyl)carbamoyl-2-pyridylmethyl]-1,3-diamopropane-2-ol obtained in Production Example 8-1 and 100 μM zinc acetate for 30 minutes. Thereafter, the gel was taken out from the solution. This gel was washed with 100 mL of 10 mM Tris-acetate buffer (pH=7.4) for 10 minutes twice. Thereafter, a fluorescent image of the gel was photographed by using a fluoro image analyzer FLA-5000 (Fuji Photo Film Co., Ltd.) at an excitation wavelength of 473 nm with use of a fluorescence detecting filter of 510 nm. Then, the gel was dyed with Coomassie brilliant blue according to a conventional dying process, and the dyed gel was photographed. The gel dyed with the zinc-complex-containing solution is referred to as "gel A", and the gel dyed with Coomassie brilliant blue is referred to as "gel B", both of which are shown in FIG. 9.

As is obvious from FIG. 9, in case that being dyed according to the conventional dyeing process, all the peptides were dyed as shown by the gel B. On the other hand, only 5: α-casein (phosphorylated), 7: β-casein (phosphorylated) and 9: pepsin (phosphorylated) to all of which the phosphoric acid has been bonded were identified exclusively, as shown by the gel A which was treated with the solution containing the inventive zinc complex. Thus, it is clear that the inventive method is advantageous in determining phosphorylated peptides exclusively in samples derived from living organisms.

This application is based on Japanese Patent Application No. 2003-56068 filed on Mar. 3, 2003, No. 2003-113707 filed on Apr. 18, 2003 and No. 2003-356934 filed on Oct. 16, 2003, the contents of which are hereby incorporated by references.

Although the present invention has been fully described by way of example, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for labeling a phosphorylated peptide comprising the step of contacting a complex compound represented by formula (I):

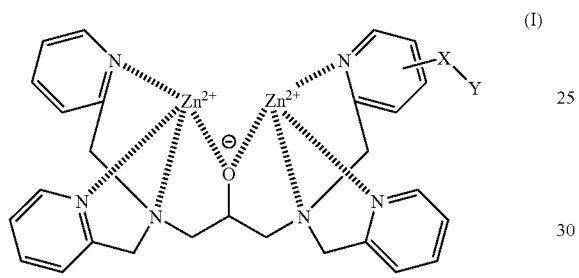

(I)

with said phosphorylated peptide, wherein X is a linker moiety, and Y is a labeling group.

2. The method according to claim 1, wherein said complex compound is a compound having biotin as the labeling group.

3. A complex compound represented by the formula (I):

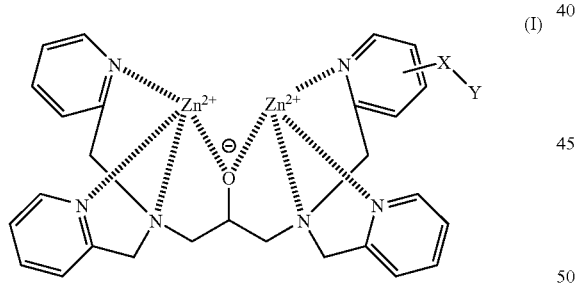

(I)

wherein X is a linker moiety, and Y is a labeling group.

4. The complex compound according to claim 3, wherein the labeling group is biotin.

5. A method for producing compound (I), comprising Scheme 1

Scheme 1

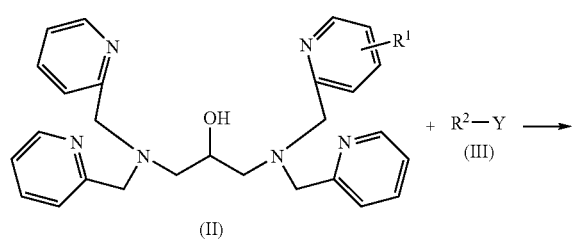

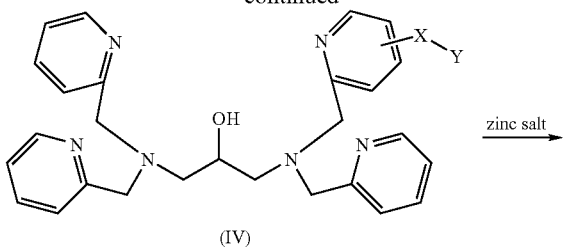

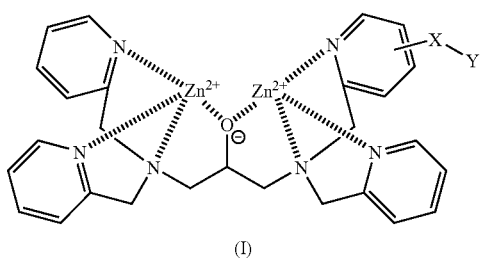

wherein, $R^1$ and $R^2$ each is a reactive group for forming the linker moiety X; wherein X is: a C1–C6 alkylene; an amino; an ether; a thioether; a carbonyl; a thionyl; an ester; an amide; a urea; a thiourea; a C1–C6 alkylene further comprising a radical selected from the group consisting of an amino, an ether, a thioether, a carbonyl, a thionyl, an ester, an amide, a urea or a thiourea at an end of the C1–C6 alkylene contacting Y or at the heterocyclic portion of Compound I; a C1–C6 alkylene further comprising two radicals selected from the group consisting of an amino, ether, a thioether, a carbonyl, a thionyl, an ester, an amide, a urea or a thiourea, wherein a first of the two radicals is at an end of the C1–C6 contacting the heterocylic portion of Compound I and a second of the two radicals is at an end of the C1–C6 alkylene contacting Y, the two radicals being identical to or different from each other; or X is a radical comprising at least two linearly linked radicals selected from the group consisting of an amino, and ether, a thioether, a carbonyl, a thionyl, an ester, an amide, a urea, a thiourea, and a C1–C6 alkylene and Y is a labeling group.

6. The method according to claim 1, wherein said complex compound is a compound having a fluorescent group as the labeling group.

7. The method according to claim 1, wherein said complex compound is a compound having a group containing an $NO_2$ radical as the labeling group.

8. The complex compound according to claim 3, wherein the labeling group is a fluorescent group.

9. The complex compound according to claim 3, wherein the labeling group is an $NO_2$ radical.

10. A precursor compound represented by formula (IV):

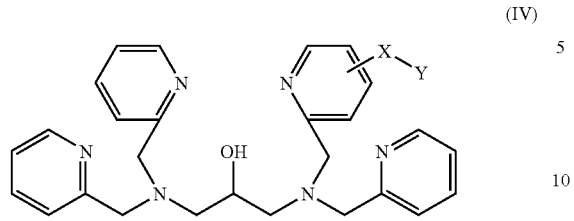

(IV)

wherein,

X is: C1–C6 alkylene; an amino; an ether; a thioether; a carbonyl; a thionyl; an ester; an amide; a urea; a thiourea; a C1–C6 alkylene further comprising a radical selected from the group consisting of an amino, an ether, a thioether, a carbonyl, a thionyl, an ester, an amide, a urea or a thiourea at an end of the C1–C6 alkylene contacting Y or at the heterocyclic portion of Compound I; a C1–C6 alkylene further comprising two radicals selected from the group consisting of an amino, ether, a thioether, a carbonyl, a thionyl, an ester, an amide, a urea or a thiourea, wherein a first of the two radicals is at an end of the C1–C6 alkylene contacting the heterocylic portion of Compound I and a second of the two radicals is at an end of the C1–C6 alkylene contacting Y, the two radicals being identical to or different from each other; or X is a radical comprising at least two linearly linked radicals selected from the group consisting of an amino, and ether, a thioether, a carbonyl, a thionyl, an ester, an amide, a urea, a thiourea, and a C1–C6 alkylene and Y is a labeling group.

* * * * *